(12) United States Patent
Aoki et al.

(10) Patent No.: US 7,420,070 B2
(45) Date of Patent: Sep. 2, 2008

(54) PROCESS FOR PREPARING OPTICALLY ACTIVE 2,3-DIHYDROBENZOFURAN COMPOUNDS

(75) Inventors: Isao Aoki, Kawanishi (JP); Mari Adachi, Kobe (JP); Hiroyuki Tawada, Takatsuki (JP); Makoto Yamashita, Amagasaki (JP); Misayo Sera, Suita (JP)

(73) Assignee: Takoda Pharmaceutical Company Limited, Osaka (JP)

( * ) Notice: Subject to any disclaimer, the term of this patent is extended or adjusted under 35 U.S.C. 154(b) by 513 days.

(21) Appl. No.: 11/054,371

(22) Filed: Feb. 9, 2005

(65) Prior Publication Data

US 2005/0171184 A1 Aug. 4, 2005

Related U.S. Application Data

(62) Division of application No. 10/451,723, filed as application No. PCT/JP01/11510 on Dec. 27, 2001, now Pat. No. 6,878,831.

(30) Foreign Application Priority Data

Dec. 28, 2000 (JP) ............................ 2000/400531

(51) Int. Cl.
*C07D 405/00* (2006.01)
*C07D 307/00* (2006.01)

(52) U.S. Cl. ...................... 549/469; 548/454; 549/467; 549/491

(58) Field of Classification Search ................ 549/469, 549/467, 491; 548/454
See application file for complete search history.

(56) References Cited

U.S. PATENT DOCUMENTS

| 4,814,477 A | 3/1989 | Wijnberg et al. |
| 5,376,681 A | 12/1994 | Aono et al. |

FOREIGN PATENT DOCUMENTS

| EP | 0180276 | 5/1988 |
| EP | 1136477 | 9/2001 |
| WO | WO 00/34262 | 6/2000 |
| WO | WO0034262 | * 6/2000 |
| WO | WO 01/30763 | 5/2001 |

OTHER PUBLICATIONS

J. Jacques et. al, *Enantiomers, Racemates, and Resolution*, (1981), pp. 387-388, John Wiley & Sons, New York, USA.

* cited by examiner

*Primary Examiner*—D. Margaret Seaman
*Assistant Examiner*—Nizal S Chandrakumar
(74) *Attorney, Agent, or Firm*—Edwards Angell Palmer & Dodge LLP; David G. Conlin; Lisa Swiszcz Hazzard

(57) ABSTRACT

A process for preparing optically active 2,3-dihydrobenzofuran compounds which comprises subjecting a 2,3-dihydrobenzofuran compound represented by the general formula or a salt thereof to optical resolution with an optically active acid compound:

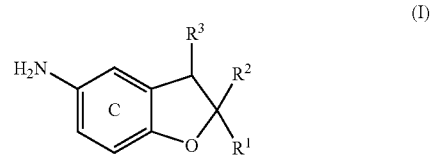

(I)

[wherein $R^1$ and $R^2$ are each hydrogen or an optionally substituted hydrocarbon group; $R^3$ is an optionally substituted aromatic group; and C is a benzene ring which may further have a substituent in addition to the amino group]. The process enables industrially advantageous production of intermediates for the synthesis of optically active 2,3-dihydrobenzofuran compounds useful as preventive and/or therapeutic drugs for neurodegenerative diseases and so on.

2 Claims, No Drawings

PROCESS FOR PREPARING OPTICALLY ACTIVE 2,3-DIHYDROBENZOFURAN COMPOUNDS

This application is a divisional of U.S. patent application Ser. No. 10/451,723 filed Jun. 24, 2003, now U.S. Pat. No. 6,878,831, issued Apr. 12, 2005, which was the National Phase filing of International Patent Application No. PCT/JP01/11510, filed Dec. 27, 2001.

TECHNICAL FIELD

The present invention provides an industrially advantageous production method for synthetic intermediates of optically active 2,3-dihydrobenzofuran derivatives that are useful as medicine for preventing or treating nerve degenerative disease and the like.

BACKGROUND ART

As a benzofuran derivative useful for the prevention or treatment of nerve degenerative diseases and the like and a production method thereof, WO00/34262 discloses, for example, a production method for (+)-2,2,4,6,7-pentamethyl-3-(4-methylphenyl)-2,3-dihydro-1-benzofuran-5-amine comprising optical resolution of 2,2,4,6,7-pentamethyl-3-(4-methylphenyl)-2,3-dihydro-1-benzofuran-5-amine by HPLC using a column for optical isomer separation.

The development for a convenient and industrially advantageous production method of a compound having antioxidant action itself, which is useful as medicine as well as a synthetic intermediate for an optically active 2,3-dihydrobenzofuran derivative useful as a medicine for preventing or treating nerve degenerative diseases and the like, have been desired.

SUMMARY OF THE INVENTION

The present inventors have conducted intensive studies on a method for optical resolution of the 2,3-dihydrobenzofuran compound or a salt thereof represented by the formula (I) mentioned below, and found that an optically active substance represented by the formula (I) or a salt thereof can be obtained in high yield and high purity, by forming a diastereomeric salt with an optically active acidic compound and then separating the compound. Based on this finding, the present invention has been completed.

Namely, the present invention provides (1) a process for producing an optically active 2,3-dihydrobenzofuran compound or a salt thereof, comprising optically resolving a 2,3-dihydrobenzofuran compound represented by the formula:

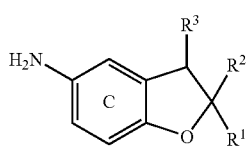

(I)

wherein $R^1$ and $R^2$ are each a hydrogen atom or an optionally substituted hydrocarbon group, $R^3$ is an optionally substituted aromatic group, ring C is a benzene ring optionally having a substituent besides the amino group or a salt thereof, with an optically active acidic compound;

(2) the process according to the above-mentioned (1), wherein $R^1$ and $R^2$ are each a $C_{1-6}$ alkyl group;

(3) the process according to the above-mentioned (1), wherein $R^3$ is a phenyl group optionally having $C_{1-6}$ alkyl and/or halogen atom;

(4) the process according to the above-mentioned (1), wherein the ring C is a benzene ring fully substituted with the substituents selected from a $C_{1-6}$ alkyl, a $C_{1-6}$ alkoxy and a $C_{1-3}$ alkylenedioxy besides the amino group;

(5) the process according to the above-mentioned (1), wherein the compound represented by the formula (I) or a salt thereof is a compound represented by the formula:

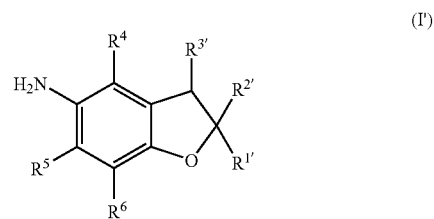

(I')

wherein $R^{1'}$ and $R^{2'}$ are each a $C_{1-6}$ alkyl group, $R^{3'}$ is a phenyl group optionally having $C_{1-6}$ alkyl and/or halogen atom, $R^4$, $R^5$ and $R^6$ are each a $C_{1-6}$ alkyl, a $C_{1-6}$ alkoxy or a $C_{1-3}$ alkylenedioxy, or a salt thereof;

(6) the process according to the above-mentioned (1), wherein the optically active acidic compound is an optically active O,O'-diacyltartaric acid derivative;

(7) the process according to the above-mentioned (1), wherein the optically active acidic compound is an optically active N-acylamino acid derivative;

(8) the process according to the above-mentioned (1), wherein the optically active acidic compound is an optically active phosphoric acid derivative represented by the formula:

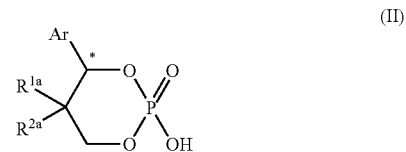

(II)

wherein Ar is an optionally substituted aromatic hydrocarbon group, $R^{1a}$ and $R^{2a}$ are each a hydrogen atom, an optionally substituted lower alkyl group, an optionally substituted lower alkoxy group, a halogen atom or a nitro group, or $R^{1a}$ and $R^{2a}$ may be together to form an optionally substituted alkylene group or an optionally substituted methylenedioxy, and the symbol * shows the position of an asymmetric carbon;

(9) the process according to the above-mentioned (1), wherein the optically active acidic compound is an optically active O,O'-di-(p-toluoyl)tartaric acid;

(10) the process according to the above-mentioned (1), wherein the optically active acidic compound is an optically active N-(3,5-dinitrobenzoyl)-α-phenylglycine;

(11) the process according to the above-mentioned (8), wherein the phosphoric acid derivative represented by the formula (II) is an optically active compound of 2-hydroxy-5,5-dimethyl-4-(1-naphthyl)-1,3,2-dioxaphosphorinane 2-oxide;

(12) the process according to the above-mentioned (5), wherein $R^4$, $R^5$ and $R^6$ are each a methyl group;

(13) a salt of a compound represented by the formula (I') with an optically active O,O'-di-(p-toluoyl)tartaric acid, an optically active N-(3,5-dinitrobenzoyl)-α-phenylglycine or an optically active 2-hydroxy-5,5-dimethyl-4-(1-naphthyl)-1,3,2-dioxaphosphorinane 2-oxide;

(14) a salt of (R)—(+)-2,2,4,6,7-pentamethyl-3-(4-methylphenyl)-2,3-dihydro-1-benzofuran-5-amine with (2S,3S)-O,O'-di-(p-toluoyl)tartaric acid;

(15) a salt of (+)-2,2,4,6,7-pentamethyl-3-[4-(1-methylethyl)phenyl]-2,3-dihydro-1-benzofuran-5-amine with (2S, 3S)-O,O'-di-(p-toluoyl)tartaric acid;

(16) a salt of (+)-2,2,4,6,7-pentamethyl-3-[4-(1-methylethyl)phenyl]-2,3-dihydro-1-benzofuran-5-amine with (S)-N-(3,5-dinitrobenzoyl)-α-phenylglycine;

(17) a salt of (+)-2,2,4,6,7-pentamethyl-3-[4-(1-methylethyl)phenyl]-2,3-dihydro-1-benzofuran-5-amine with (+)-2-hydroxy-5,5-dimethyl-4-(1-naphthyl)-1,3,2-dioxaphosphorinane2-oxide;

(18) a salt of (+)-2,2,4,6,7-pentamethyl-3-(4-bromophenyl)-2,3-dihydro-1-benzofuran-5-amine with (2S,3S)-O,O'-di-(p-toluoyl)tartaric acid;

(19) a process for preparing a compound represented by the formula:

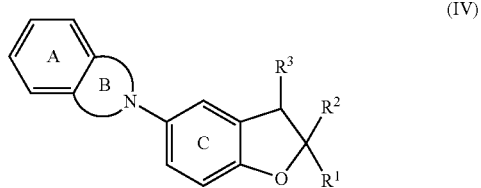

wherein $R^1$ and $R^2$ are each a hydrogen atom or an optionally substituted hydrocarbon group, $R^3$ is an optionally substituted aromatic group, ring A is an optionally substituted benzene ring, ring B is a 5- to 7-membered nitrogen-containing heterocyclic ring optionally substituted with a halogen or an optionally substituted hydrocarbon group, ring C is a benzene ring optionally having substituent besides the amino group, or a salt thereof, comprising optically resolving a 2,3-dihydrobenzofuran compound represented by the formula:

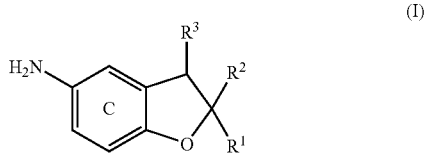

wherein the symbols are as defined above, or a salt thereof with an optically active acidic compound to give a compound represented by the formula:

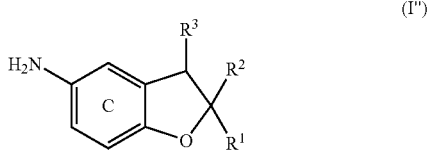

wherein the symbols are as defined above, or a salt thereof, and reacting the obtained compound (I'') with a compound represented by the formula:

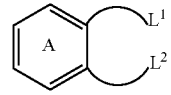

wherein $L^1$ and $L^2$ are each a leaving group and the ring A is as defined above, or a salt thereof, optionally in the presence of a base;

(20) the process according to the above-mentioned (19), wherein the ring B is a 5-membered nitrogen-containing heterocyclic ring; and

(21) the process according to the above-mentioned (19), wherein (R)—(+)-5,6-dimethoxy-2-[2,2,4,6,7-pentamethyl-3-(4-methylphenyl)-2,3-dihydro-1-benzofuran-5-yl]isoindoline (also referred to as (R)-5,6-dimethoxy-2-[2,2,4,6,7-pentamethyl-3-(4-methylphenyl)-benzofuran-5-yl]-2,3-dihydro-1H-isoindole, and so forth), (R)—(+)-5,6-dimethoxy-2-[2,2,4,6,7-pentamethyl-3-(1-methylethylphenyl)-2,3-dihydro-1-benzofuran-5-yl] isoindoline or (R)—(+)-5,6-dimethoxy-2-[2,2,4,6,7-pentamethyl-3-(4-bromophenyl)-2,3-dihydro-1-benzofuran-5-yl]isoindoline, or a salt thereof is produced.

According to the present invention, the resolution of optical isomers at the 3-position apart from the amino group substituted at the 5-position of the benzofuran ring, become possible by using the present optically active acidic compound.

DETAILED DESCRIPTION OF THE INVENTION

In the above-mentioned formula, $R^1$ and $R^2$ are each a hydrogen atom or an optionally substituted hydrocarbon group.

The "hydrocarbon group" of the "optionally substituted hydrocarbon group" represented by $R^1$ or $R^2$ includes for example a chain or cyclic hydrocarbon group (e.g., alkyl, alkenyl, alkynyl, cycloalkyl, aryl and the like) and the like. Of these, a chain or cyclic hydrocarbon group having 1 to 16 carbon atoms and the like are preferred.

As the "alkyl", for example, a $C_{1-6}$ alkyl (e.g., methyl, ethyl, propyl, isopropyl, butyl, isobutyl, sec-butyl, tert-butyl, pentyl, hexyl and the like) and the like are preferred.

As the "alkenyl", for example, a $C_{2-6}$ alkenyl (e.g., vinyl, allyl, isopropenyl, butenyl, isobutenyl, sec-butenyl and the like) and the like are preferred.

As the "alkynyl", for example, a $C_{2-6}$ alkynyl (e.g., ethynyl, propargyl, butynyl, 1-hexynyl and the like) and the like are preferred.

As the "cycloalkyl", for example, a $C_{3-6}$ cycloalkyl (e.g., cyclopropyl, cyclobutyl, cyclopentyl, cyclohexyl and the like) and the like are preferred.

As the "aryl", for example, a $C_{6-14}$ aryl (e.g., phenyl, 1-naphthyl, 2-naphthyl, biphenylyl, 2-anthryl and the like) and the like are preferred.

The "substituent" of the "optionally substituted hydrocarbon group" represented by $R^1$ or $R^2$ includes for example (1) a halogen atom (e.g., fluorine, chlorine, bromine, iodine and the like), (2) a $C_{1-3}$ alkylenedioxy (e.g., methylenedioxy, ethylenedioxy and the like), (3) a nitro, (4) a cyano, (5) an optionally halogenated $C_{1-6}$ alkyl, (6) an optionally halogenated $C_{2-6}$ alkenyl, (7) an optionally halogenated $C_{2-6}$ alkynyl, (8) an optionally halogenated $C_{3-6}$ cycloalkyl, (9) a $C_{6-14}$ aryl (e.g., phenyl, 1-naphthyl, 2-naphthyl, biphenylyl, 2-anthryl and the like), (10) an optionally halogenated $C_{1-6}$ alkoxy, (11) an optionally halogenated $C_{1-6}$ alkylthio or mercapto, (12) a hydroxy, (13) an amino, (14) a mono-$C_{1-6}$ alkylamino (e.g., methylamino, ethylamino and the like), (15) a mono-$C_{6-14}$ arylamino (e.g., phenylamino, 1-naphthylamino, 2-naphthylamino and the like), (16) a di-$C_{1-6}$ alkylamino (e.g., dimethylamino, diethylamino and the like), (17) a di-$C_{6-14}$ arylamino (e.g., diphenylamino and the like), (18) an acyl, (19) an acylamino, (20) an acyloxy, (21) a 5- to 7-membered saturated cyclic amino optionally having substituent, (22) a 5- to 10-membered aromatic heterocyclic group (e.g., 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl and the like), (23) a sulfo, (24) a $C_{6-14}$ aryloxy (e.g., phenyloxy, naphthyloxy and the like), and the like.

The "hydrocarbon group" may have, for example, 1 to 5, preferably 1 to 3 of the above-mentioned substituents at the substitutable position, and when the number of the substituents is two or more, the substituents may be the same or different.

The above-mentioned "optionally halogenated $C_{1-6}$ alkyl" includes for example a $C_{1-6}$ alkyl (e.g., methyl, ethyl, propyl, isopropyl, butyl, isobutyl, sec-butyl, tert-butyl, pentyl, hexyl and the like) optionally having 1 to 5, preferably 1 to 3 halogen atoms (e.g., fluorine, chlorine, bromine, iodine and the like) and the like. Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

The above-mentioned "optionally halogenated $C_{2-6}$ alkenyl" includes for example a $C_{2-6}$ alkenyl (e.g., vinyl, allyl, isopropenyl, butenyl, isobutenyl, sec-butenyl and the like) optionally having 1 to 5, preferably 1 to 3 halogen atoms (e.g., fluorine, chlorine, bromine, iodine and the like) and the like. Specific examples include vinyl, allyl, isopropenyl, butenyl, isobutenyl, sec-butenyl, 3,3,3-trifluoro-1-propenyl, 4,4,4-trifluoro-1-butenyl and the like.

The above-mentioned "optionally halogenated $C_{2-6}$ alkynyl" includes for example a $C_{2-6}$ alkynyl (e.g., ethynyl, propargyl, butynyl, 1-hexynyl and the like) optionally having 1 to 5, preferably 1 to 3 halogen atoms (e.g., fluorine, chlorine, bromine, iodine and the like) and the like. Specific examples include ethynyl, propargyl, butynyl, 1-hexynyl, 3,3,3-trifluoro-1-propynyl, 4,4,4-trifluoro-1-butynyl and the like.

The above-mentioned "optionally halogenated $C_{3-6}$ cycloalkyl" includes for example a $C_{3-6}$ cycloalkyl (e.g., cyclopropyl, cyclobutyl, cyclopentyl, cyclohexyl and the like) optionally having 1 to 5, preferably 1 to 3 halogen atoms (e.g., fluorine, chlorine, bromine, iodine and the like) and the like. Specific examples include cyclopropyl, cyclobutyl, cyclopentyl, cyclohexyl, 4,4-dichlorocyclohexyl, 2,2,3,3-tetrafluorocyclopentyl, 4-chlorocyclohexyl and the like.

The above-mentioned "optionally halogenated $C_{1-6}$ alkoxy" includes for example a $C_{1-6}$ alkoxy (e.g., methoxy, ethoxy, propoxy, isopropoxy, butoxy, isobutoxy, sec-butoxy, pentyloxy, hexyloxy and the like) optionally having 1 to 5, preferably 1 to 3 halogen atoms (e.g., fluorine, chlorine, bromine, iodine and the like) and the like. Specific examples include for example methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like.

The above-mentioned "optionally halogenated $C_{1-6}$ alkylthio" includes for example a $C_{1-6}$ alkylthio (e.g., methylthio, ethylthio, propylthio, isopropylthio, butylthio, sec-butylthio, tert-butylthio and the like) optionally having 1 to 5, preferably 1 to 3 halogen atoms (e.g., fluorine, chlorine, bromine, iodine and the like) and the like. Specific examples include methylthio, difluoromethylthio, trifluoromethylthio, ethylthio, propylthio, isopropylthio, butylthio, 4,4,4-trifluorobutylthio, pentylthio, hexylthio and the like.

The above-mentioned "acyl" includes for example formyl, carboxy, carbamoyl, a $C_{1-6}$ alkyl-carbonyl (e.g., acetyl, propionyl and the like), a $C_{3-6}$ cycloalkyl-carbonyl (e.g., cyclopropylcarbonyl, cyclopentylcarbonyl, cyclohexylcarbonyl and the like), a $C_{1-6}$ alkoxy-carbonyl (e.g., methoxycarbonyl, ethoxycarbonyl, propoxycarbonyl, tert-butoxycarbonyl and the like), a $C_{6-14}$ aryl-carbonyl (e.g., benzoyl, 1-naphthoyl, 2-naphthoyl and the like), a $C_{7-16}$ aralkyl-carbonyl (e.g., phenylacetyl, phenylpropionyl and the like), a $C_{6-14}$ aryloxy-carbonyl (e.g., phenoxycarbonyl and the like), a $C_{7-16}$ aralkyloxy-carbonyl (e.g., benzyloxycarbonyl, phenethyloxycarbonyl and the like), a 5- or 6-membered heterocyclic carbonyl (e.g., nicotinoyl, isonicotinoyl, 2-thenoyl, 3-thenoyl, 2-furoyl, 3-furoyl, morpholinocarbonyl, thiomorpholinocarbonyl, piperidinocarbonyl, 1-pyrrolidinylcarbonyl and the like), a mono-$C_{1-6}$ alkyl-carbamoyl (e.g., methylcarbamoyl, ethylcarbamoyl and the like), a di-$C_{1-6}$ alkyl-carbamoyl (e.g., dimethylcarbamoyl, diethylcarbamoyl, ethylmethylcarbamoyl and the like), a $C_{6-14}$ aryl-carbamoyl (e.g., phenylcarbamoyl, 1-naphthylcarbamoyl, 2-naphthylcarbamoyl and the like), a thiocarbamoyl, a 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl and the like), a $C_{1-6}$ alkylsulfonyl (e.g., methylsulfonyl, ethylsulfonyl and the like), a $C_{6-14}$ arylsulfonyl (e.g., phenylsulfonyl, 1-naphthylsulfonyl, 2-naphthylsulfonyl and the like), a $C_{1-6}$ alkylsulfinyl (e.g., methylsulfinyl, ethylsulfinyl and the like), a $C_{6-14}$ arylsulfinyl (e.g., phenylsulfinyl, 1-naphthylsulfinyl, 2-naphthylsulfinyl and the like) and the like.

The above-mentioned "acylamino" includes for example a formylamino, a $C_{1-6}$ alkyl-carbonylamino (e.g., acetylamino and the like), a $C_{6-14}$ aryl-carbonylamino (e.g., phenylcarbonylamino, naphthylcarbonylamino and the like), a $C_{1-6}$ alkoxy-carbonylamino (e.g., methoxycarbonylamino, ethoxycarbonylamino, propoxycarbonylamino, butoxycarbonylamino and the like), a $C_{1-6}$ alkylsulfonylamino (e.g., methylsulfonylamino, ethylsulfonylamino and the like), a $C_{6-14}$ arylsulfonylamino (e.g., phenylsulfonylamino, 2-naphthylsulfonylamino, 1-naphthylsulfonylamino and the like) and the like.

The above-mentioned "acyloxy" includes for example a $C_{1-6}$ alkyl-carbonyloxy (e.g., acetoxy, propionyloxy and the like), a $C_{6-14}$ aryl-carbonyloxy (e.g., benzoyloxy, naphthylcarbonyloxy and the like), a $C_{1-6}$ alkoxy-carbonyloxy (e.g., methoxycarbonyloxy, ethoxycarbonyloxy, propoxycarbonyloxy, butoxycarbonyloxy and the like), a mono-$C_{1-6}$ alkyl-carbamoyloxy (e.g., methylcarbamoyloxy, ethylcarbamoyloxy and the like), a di-$C_{1-6}$ alkyl-carbamoyloxy (e.g., dimethylcarbamoyloxy, diethylcarbamoyloxy and the like), a $C_{6-14}$ aryl-carbamoyloxy (e.g., phenylcarbamoyloxy, naphthylcarbamoyloxy and the like), a nicotinoyloxy and the like.

The "5- to 7-membered saturated cyclic amino" of the above-mentioned "5- to 7-membered saturated cyclic amino optionally having substituent" includes for example morpholino, thiomorpholino, piperazin-1-yl, piperidino, pyrrolidin-1-yl and the like. The "substituent" of the "5- to 7-membered saturated cyclic amino optionally having substituent" includes 1 to 3 substituents such as a $C_{1-6}$ alkyl (e.g., methyl, ethyl, propyl, isopropyl, butyl, isobutyl, sec-butyl, tert-butyl, pentyl, hexyl and the like), a $C_{6-14}$ aryl (e.g., phenyl, 1-naphthyl, 2-naphthyl, biphenylyl, 2-anthryl and the like), a 5- to 10-membered aromatic heterocyclic group (e.g., 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl and the like) and the like.

Preferably, $R^1$ and $R^2$ are a $C_{1-6}$ alkyl group such as methyl and the like.

$R^3$ is an optionally substituted aromatic group.

The "aromatic group" includes aromatic hydrocarbon group, aromatic heterocyclic group and the like.

The "aromatic hydrocarbon group" includes for example a monocyclic or fused polycyclic (bicyclic or tricyclic) aromatic hydrocarbon group having 6 to 14 carbon atoms and the like. Specific examples thereof include a $C_{6-14}$ aryl such as phenyl, 1-naphthyl, 2-naphthyl, biphenylyl, anthryl and the like, preferably a $C_{6-10}$ aryl such as phenyl, 1-naphthyl, 2-naphthyl and the like.

The "aromatic heterocyclic group" includes for example a 5- to 14-membered, preferably 5- to 10-membered aromatic heterocyclic group containing one or more (e.g., 1 to 4) heteroatoms selected from a nitrogen atom, a sulfur atom and an oxygen atom besides carbon atoms. Specific examples thereof include for example an aromatic heterocyclic ring such as thiophene, benzothiophene, benzofuran, benzimidazole, benzoxazole, benzothiazole, benzisothiazole, naphtho[2,3-b]thiophene, furan, isoindolidine, xanthrene, phenoxathiine, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, oxazole, isoxazole, furazane, phenoxazine and the like, or a monovalent group formed by removing any hydrogen atom from a ring formed by condensation of the above-mentioned ring (preferably monocyclic ring) with one or more (preferably 1 or 2) of aromatic rings (e.g., benzene ring and the like) and the like.

As the "substituent" of the "optionally substituted aromatic group", the substituents and the number thereof are exemplified by those for the "optionally substituted hydrocarbon group" represented by $R^1$ or $R^2$ mentioned above.

$R^3$ is preferably a phenyl group optionally having 1 to 3 of $C_{1-6}$ alkyl and/or halogen atom, and more preferably a phenyl group optionally having $C_{1-6}$ alkyl or halogen atom at the para position. The "$C_{1-6}$ alkyl" of "a phenyl group optionally having $C_{1-6}$ alkyl and/or halogen atom" includes, as mentioned above, for example methyl, ethyl, propyl, isopropyl, butyl, isobutyl, sec-butyl, tert-butyl, pentyl, hexyl and the like, and the "halogen atom" includes for example fluorine, chlorine, bromine, iodine and the like.

The ring C optionally has 1 to 3 (preferably 3) substituents at the substitutable position besides the amino group, and when the number of the substituent is two or more, the substituents may be the same or different.

As the "substituent" that the ring C may further have, the substituents and the number thereof are exemplified by those for the "substituents" of the "optionally substituted hydrocarbon group" represented by the above-mentioned $R^1$ or $R^2$.

The ring C is preferably a benzene ring fully substituted with substituents selected from a $C_{1-6}$ alkyl, a $C_{1-6}$ alkoxy and a $C_{1-3}$ alkylenedioxy besides the amino group. Specifically, a benzene ring having three $C_{1-6}$ alkyls such as methyl and the like is preferred.

In the above-mentioned formula, the "$C_{1-6}$ alkyl group" represented by $R^{1'}$, $R^{2'}$, $R^{3'}$, $R^4$, $R^5$ or $R^6$ and "$C_{1-6}$ alkoxy group" represented by $R^4$, $R^5$ or $R^6$ include groups similar to those exemplified for the above-mentioned $R^1$, $R^2$ and $R^3$.

The "$C_{1-3}$ alkylenedioxy" represented by $R^4$, $R^5$ and $R^6$ include for example methylenedioxy, ethylenedioxy and the like.

Preferably, $R^4$, $R^5$ and $R^6$ are a $C_{1-6}$ alkyl group such as methyl and the like.

The salt of the compound represented by the formula (I) and (I') includes for example a salt with an inorganic acid, a salt with an organic acid, a salt with an amino acid and the like. Preferred examples of the salt with an inorganic acid includes for example a salt with hydrochloric acid, hydrobromic acid, nitric acid, sulfuric acid or phosphoric acid or the like. Preferred examples of the salt with an organic acid includes for example a salt with formic acid, acetic acid, trifluoroacetic acid, fumaric acid, oxalic acid, tartaric acid, maleic acid, citric acid, succinic acid, malic acid, methanesulfonic acid, benzenesulfonic acid or p-toluenesulfonic acid or the like. Preferred examples of the salt with an amino acid include for example a salt with aspartic acid, glutamic acid, glycine or alanine or the like.

In the production method of the present invention, an optically active form of the compound represented by the above-mentioned formula (I) or a salt thereof [hereinafter sometimes referred to as an optically active form of a compound (I)] can be produced by converting the 2,3-dihydrobenzofuran compound or a salt thereof represented by the formula (I) [hereinafter sometimes referred to as a compound (I)] into a salt with an optically active acidic compound and subjecting the salt to optical resolution.

The optical resolution of the optical isomer mixture (I) of the 2,3-dihydrobenzofuran derivative with an optically active acidic compound can be carried out, for example, according to the following operations.

Firstly, the (I) and an optically active acidic compound which is an acidic resolution agent, are reacted in a suitable solution to form a diastereomeric salt.

The optically active acidic compound includes, for example, an optically active tartaric acid derivative such as an optically active O,O'-di-acyltartaric acid derivative, for example, an optically active amino acid derivative such as an optically active N-acylamino acid, and for example, an optically active phosphoric acid derivative such as a compound represented by the formula (II), and the like. The preferred acyl group for the O,O'-di-acyltartaric acid derivative include a lower ($C_{1-6}$)alkanoyl group such as acetyl, propionyl, butyryl, valeryl and the like, and an aroyl group such as benzoyl, p-chlorobenzoyl, naphthoyl and the like. The most preferable O,O'-di-acyltartaric acid is O,O'-di-(p-toluoyl)tartaric acid.

The preferable N-acyl group for the N-acylamino acid derivative includes a lower ($C_{1-6}$)alkanoyl group such as acetyl, propionyl, butyryl, valeryl and the like, an aroyl group such as benzoyl, p-chlorobenzoyl, naphthoyl and the like. The amino acid includes for example α-phenylglycine. The most preferable N-acylamino acid derivative is N-(3,5-dinitrobenzoyl)-α-phenylglycine.

The optically active phosphoric acid derivative represented by the formula (II) can be obtained easily according to the methods disclosed in JP-A S61-103886, J. Org. Chem., 50, 4508 (1985) and the like, and some compounds are readily available as commercial products. Specifically, for example, 2-hydroxy-5,5-dimethyl-4-phenyl-1,3,2-dioxaphosphorinane 2-oxide, 4-(2-chlorophenyl)-2-hydroxy-5,5-dimethyl-1,3,2-dioxaphosphorinane 2-oxide, 4-(2,4-dichlorophenyl)-2-hydroxy-5,5-dimethyl-1,3,2-dioxaphosphorinane 2-oxide, 2-hydroxy-4-(2-methoxyphenyl)-5,5-dimethyl-1,3,2-dioxaphosphorinane 2-oxide, 2-hydroxy-5,5-dimethyl-4-(1-naphthyl)-1,3,2-dioxaphosphorinane-2-oxide and the like are exemplified.

The "aromatic hydrocarbon group" of the "optionally substituted aromatic hydrocarbon group" represented by Ar includes a $C_{6-14}$ aryl (e.g., phenyl, naphthyl and the like) and the like. The "substituent" of the "optionally substituted aromatic hydrocarbon group" includes the same number and the same substituents as those exemplified for the "substituent" of the above-mentioned "optionally substituted hydrocarbon group" represented by $R^1$ or $R^2$. The "substituent" preferably includes 1 to 2 substituents selected from a $C_{1-6}$ alkyl group such as methyl, ethyl and the like, a $C_{1-6}$ alkoxy group such as methoxy, ethoxy and the like, a halogen atom such as fluorine, chlorine, bromine and the like.

The "lower alkyl group" of the "optionally substituted lower alkyl group" represented by $R^{1a}$ and $R^{2a}$ includes for example a $C_{1-6}$ alkyl (e.g., methyl, ethyl, propyl, isopropyl, butyl, isobutyl, sec-butyl, tert-butyl, pentyl, hexyl and the like) and the like. The "substituent" of the "optionally substituted lower alkyl group" includes the same number and the same substituents as those exemplified for the "substituent" of the above-mentioned "optionally substituted hydrocarbon group" represented by $R^1$ or $R^2$. The "substituent" preferably includes 1 to 2 substituents selected from a halogen atom (e.g., fluorine, chlorine, bromine and the like), nitro, cyano, a $C_{1-4}$ alkanoyl (e.g., acetyl, propionyl and the like), a carboxyl, a $C_{1-4}$ alkoxy (e.g., methoxy, ethoxy, propoxy and the like), a $C_{1-4}$ alkoxy-carbonyl (e.g., methoxycarbonyl, ethoxycarbonyl, butoxycarbonyl and the like), a carbamoyl, a $C_{1-4}$ alkoxy-carbonylamino (e.g., methoxycarbonylamino, ethoxycarbonylamino and the like) and the like.

The "lower alkoxy group" of the "optionally substituted lower alkoxy group" represented by $R^{1a}$ and $R^{2a}$ includes for example a $C_{1-6}$ alkoxy (e.g., methoxy, ethoxy, propoxy, isopropoxy, butoxy, isobutoxy, sec-butoxy, pentyloxy, hexyloxy and the like) and the like. The "substituent" of the "optionally substituted lower alkoxy group" includes the same number and the same substituents as those exemplified for the "substituent" of the above-mentioned "optionally substituted hydrocarbon group" represented by $R^1$ or $R^2$. The "substituent" preferably includes 1 to 2 substituents selected from a $C_{1-4}$ alkanoyl (e.g., acetyl, propionyl and the like), carboxyl, hydroxy group, a $C_{1-4}$ alkoxy (e.g., methoxy, ethoxy, propoxy and the like), a $C_{1-4}$ alkoxy-carbonyl (e.g., methoxycarbonyl, ethoxycarbonyl, butoxycarbonyl and the like) and the like.

The "halogen atom" represented by $R^{1a}$ and $R^{2a}$ includes fluorine, chlorine, bromine, iodine and the like.

When the $R^{1a}$ and $R^{2a}$ are together to represent an optionally substituted alkylene group, the optionally substituted alkylene group includes an unsubstituted alkylene having 2 to 6 carbons (dimethylene, trimethylene, tetramethylene, pentamethylene) and a group having 1 or 2 substituents selected from lower alkyl group (e.g., a $C_{1-4}$ alkyl such as methyl, ethyl, propyl and the like), lower alkoxy group (e.g., a $C_{1-4}$ alkoxy such as methoxy, ethoxy, propoxy and the like), nitro group, a halogen atom (e.g., fluorine, chlorine, bromine, iodine) and the like at any position of these alkylene.

When the $R^{1a}$ and $R^{2a}$ are together to represent an optionally substituted methylenedioxy group, the methylene group thereof may be substituted with, for example a halogen atom (e.g., fluorine, chlorine, bromine, iodine), a nitro group and the like.

The preferable examples of $R^{1a}$ and $R^{2a}$ include the case in which both $R^{1a}$ and $R^{2a}$ are methyl group, and the case in which both are bound together to represent a tetramethylene group.

Of the optically active phosphoric acid derivatives represented by the formula (II), 2-hydroxy-5,5-dimethyl-4-(1-naphthyl)-1,3,2-dioxaphosphorinane 2-oxide is most preferred.

The amount of the acidic resolution agent to be used is 0.1 to 4-fold mol, preferably 0.6 to 2.5-fold mol relative to the (I). In addition, on this occasion, a mineral acid such as hydrochloric acid, sulfuric acid, phosphoric acid and the like or an organic acid such as acetic acid, propionic acid, fumaric acid, maleic acid and the like may be co-existed with the resolution agent in a such a way that the amount of acids including resolution agent are in the above-mentioned mol range.

The solvent to be used is preferably a solvent which does not chemically change the (I) and the acidic resolution agent and hardly dissolves one of the diastereomeric salts formed. For example, water, alcohols such as methanol, ethanol, isopropanol and the like, ethers such as diethylether, diisopropylether, 1,2-dimethoxyethane, tetrahydrofuran, tetrahydropyran and the like, ketones such as acetone, 2-butanone and the like, nitriles such as acetonitrile and the like, aromatic hydrocarbons such as benzene, toluene, are exemplified. One of these solvents can be used solely, or two or more of them can be used as a mixture. The amount of the solvent to be used is generally 1 to 1000-fold amounts, preferably 1 to 100-fold amounts relative to the (I). The temperature is generally not less than 15° C., and may be in the range not more than the boiling point of the solvent to be used.

After the formation of the diastereomeric salts, one of the salts can be crystallized out by cooling or concentration. In a certain condition, a hardly-soluble salt is readily crystallized out by leaving or stirring under the room temperature, without operation such as cooling or concentration.

The crystallized salt can be readily separated by a general solid-liquid separation method such as filtration, centrifugation and the like. Furthermore, the purity of the separated salt crystals can be enhanced by a method known per se such as recrystallization and the like, if necessary.

After the separation of the hardly-soluble salt, the mother liquor as it is sometimes contains only an readily-soluble salt. The readily-soluble salt can be separated as it is, or by concentration and the subsequent cooling.

Of the obtained salts, a salt of a compound represented by the formula (I') with an optically active O,O'-di-(p-toluoyl) tartaric acid, an optically active N-(3,5-dinitrobenzoyl)-α-phenylglycine or an optically active form of 2-hydroxy-5,5-dimethyl-4-(1-naphthyl)-1,3,2-dioxaphosphorinane 2-oxide, and specifically a salt of (R)—(+)-2,2,4,6,7-pentamethyl-3-(4-methylphenyl)-2,3-dihydro-1-benzofuran-5-amine with (2S,3S)-O, O'-di-(p-toluoyl)tartaric acid, a salt of (+)-2,2,4,6,7-pentamethyl-3-[4-(1-methylethyl)phenyl]-2,3-dihydro-1-benzofuran-5-amine with (2S,3S)-O, O'-di-(p-toluoyl)tartaric acid, a salt of (+)-2,2,4,6,7-pentamethyl-3-[4-(1-methylethyl)phenyl]-2,3-dihydro-1-benzofuran-5-amine with (S)—N—(3, 5-dinitrobenzoyl)-α-phenylglycine, a salt of (+)-2,2,4,6,7-pentamethyl-3-[4-(1-methylethyl)phenyl]-2,3-dihydro-1-benzofuran-5-amine with (+)-2-hydroxy-5,5-dimethyl-4-(1-naphthyl)-1,3,2-dioxaphosphorinane2-oxide, and a salt of (+)-2,2,4,6,7-pentamethyl-3-(4-bromophenyl)-2,3-dihydro-1-benzofuran-5-amine with (2S,3S)—O,O'-di-(p-toluoyl)tartaric acid, are novel salts.

For the decomposition of the thus-obtained salt, any known methods may be used. For example, the object can be achieved by the treatment with an alkaline or an acid in a aqueous solution. The free optically active 2,3-dihydrobenzofuran compound can be isolated by treating the salt with aqueous base such as an aqueous solution of sodium hydroxide, sodium hydrogencarbonate and the like, and successively separating by solid-liquid separation method such as filtration, centrifugation and the like or extracting with an organic solvent and the like. The treatment with a base is generally carried out at about −10 to 25° C., and the amount of the base to be used is 1 to 5-fold mol relative to the diastereomeric salts. The concentration of such base is 1 to 50 wt %, preferably 5 to 20 wt %.

The basic water layer after the separation of the optically active 2,3-dihydrobenzofuran compound may be made acidic with an acid such as hydrochloric acid, sulfuric acid and the like to recover the resolution agent, and the recovered agent can be reused.

The thus-obtained optically active 2,3-dihydrobenzofuran compound can be used as a reaction solution as it is, or can be used in the next reaction as a crude substance, or can be used after purification by a general separation mean (e.g., recrystallization, distillation, chromatography and the like).

As mentioned above, according to the production method of the present invention, the resolution of optical isomers at the 3-position apart from the amino group substituted at the 5-position of the benzofuran ring becomes possible, using the optically active acidic compound.

In the above-mentioned production method, while the compound(I) used as a starting material can be produced by a method disclosed in WO00/34262 or a similar method thereto, it can be produced by the following method.

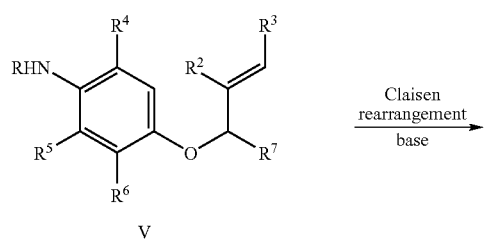

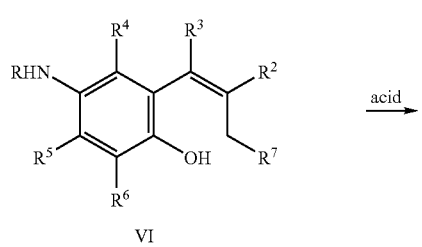

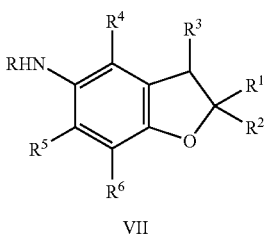

wherein $R^7$ is a hydrogen atom or a group formed by removing one methylene group from $R^1$, and the other symbols are as defined above.

The compound (VI) can be produced by Claisen rearrangement of the compound (V). This reaction is advantageously carried out under the presence of a base catalyst without solvent or in a solvent inert to the reaction. As the base catalyst, for example, carbonate alkaline metal salts such as sodium hydrogencarbonate, potassium hydrogencarbonate, sodium carbonate, potassium carbonate, cesium carbonate and the like, amines such as triethylamine, N-ethyldiisopropylamine, DBU (1,8-diazabicyclo[5.4.0]-7-undecene), DBN (1,5-diazabicyclo[4.3.0]-5-nonene) and the like, are preferably used. The amount of the base catalyst to be used is 0.01 mol % to 5 mol %, preferably 0.1 mol % to 3 mol % relative to 1 mol of the compound (V). As the solvent, which is not specifically limited as long as the reaction proceeds, for example, alcohols such as methanol, ethanol, propanol and the like, hydrocarbons such as cyclohexane, hexane, benzene, toluene, xylene, mesitylene and the like, ethers such as tetrahydrofuran, dioxane, 1,2-dimethoxyethane, diethylether, diisopropylether and the like, anilines such as N,N-dimethylaniline, N,N-diethylaniline and the like, halogenated hydrocarbons such as dichloromethane, chloroform, carbon tetrachloride, 1,2-dichloroethane and the like, or a mixed solvent thereof, are used.

The reaction period is generally about 30 min to 24 hr, preferably 1 hr to 12 hr. The reaction temperature is generally 50° C. to 350° C., preferably 150° C. to 220° C.

The compound (VII) is produced by ring-closure of the compound (VI) in the presence of an acid.

As the acid, mineral acids such as hydrochloric acid, hydrobromic acid, sulfuric acid and the like, sulfonic acids such as p-toluenesulfonic acid, camphorsulfonic acid and the like, Lewis acids such as aluminum chloride, boron trifluoride and the like are used.

The amount of the acid to be used is generally 1 to 500 mol, preferably 5 to 200 mol relative to 1 mol of the compound (VI).

In this reaction, while the acid to be used may be also used as a solvent, it is advantageous to use an inert solvent to this reaction. Such solvent is not specifically limited as long as the reaction proceeds, and for example, alcohols such as methanol, ethanol, propanol, butanol, isobutanol, methoxyethanol and the like, hydrocarbons such as cyclohexane, hexane, benzene, toluene, xylene, mesitylene and the like, ethers such as tetrahydrofuran, dioxane, 1,2-dimethoxyethane, diethylether, diisopropylether and the like, amides such as N,N- dimethylformamide, N,N-dimethylacetamide, hexamethylphosphoramide and the like, sulfoxides such as dimethylsulfoxide and the like, halogenated hydrocarbons such as dichloromethane, chloroform, carbon tetrachloride, 1,2-dichloroethane and the like, or a mixed solvent thereof, are used.

The reaction period is generally about 30 min to 24 hr, preferably 1 hr to 12 hr. The reaction temperature is generally 0° C. to 200° C., preferably 10° C. to 180° C.

The compound represented by the formula:

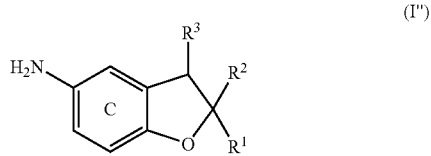

(I''')

wherein the symbols in the formula are as defined above, or a salt thereof (hereinafter sometimes referred to as a compound (I''')), which is one of the enantiomers of the optically active 2,3-dihydrobenzofuran compound obtained by the production method of the present invention, is useful as a medicine itself, and is also useful as a synthetic starting material or synthetic intermediate for the production of an optically active medicine. For example, according to the method disclosed in WO00/34262, a compound represented by the formula:

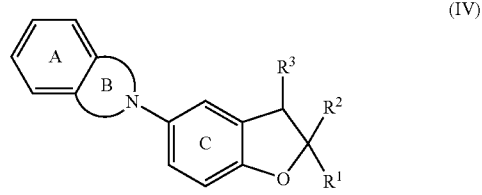

(IV)

wherein ring A is an optionally substituted benzene ring, ring B is 5- to 7-membered nitrogen-containing heterocyclic ring optionally substituted with a halogen or an optionally substituted hydrocarbon group, and the other symbols are as defined above or a salt thereof (hereinafter sometimes referred to as a compound (IV)), which is obtained by reacting the compound (I''') obtained by the production method of the present invention and a compound represented by the formula:

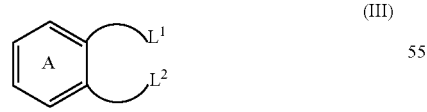

(III)

wherein ring A is as defined above, and $L^1$ and $L^2$ are each a leaving group or a salt thereof (hereinafter sometimes referred to as a compound (III)) optionally in the presence of a base, has superior medical actions such as neurotrophic factor-like action, neurotrophic factor activity-enhancing action, nerve degeneration-suppressing action, nerve regeneration-accelerating action, antioxidant action or a suppressing action for nerve cell death due to β amyloid and the like, and also has superior characteristics such as low toxicity, decreased side effect and the like, and is useful as a pharmaceutical agent.

In the compounds (III) and (IV), as the substituents of the "optionally substituted benzene ring" represented by the ring A, ring A may have 1 to 4 (preferably 1 or 2) substituents exemplified by the "substituent" for the "optionally substituted hydrocarbon group" represented by the above-mentioned $R^1$ or $R^2$ at the substitutable position of the ring, and when the number of the substituent is two or more, the substituent may be the same or different.

In the compound (IV), the "5- to 7-membered nitrogen-containing heterocyclic ring" represented by the ring B includes a 5- to 7-membered nitrogen-containing heterocyclic ring such as pyrrole (e.g., 1H-pyrrole and the like), dihydropyrrole (e.g., 2,5-dihydro-1H-pyrrole and the like), dihydropyridine (e.g., 1,2-dihydropyridine and the like), tetrahydropyridine (e.g., 1,2,3,4-tetrahydropyridine and the like), azepine (e.g., 1H-azepine and the like), dihydroazepine (e.g., 2,3-dihydro-1H-azepine, 2,5-dihydro-1H-azepine, 2,7-dihydro-1H-azepine and the like), tetrahydroazepine (e.g., 2,3,6,7-tetrahydro-1H-azepine, 2,3,4,7-tetrahydro-1H-azepine and the like) and the like.

The "halogen" as the "substituents" that the ring B may have includes for example fluorine, chlorine, bromine, iodine and the like.

The "optionally substituted hydrocarbon group" as the substituent that the ring B may have includes those exemplified by the "optionally substituted hydrocarbon group" represented by the above-mentioned $R^1$ or $R^2$.

The ring B may have 1 to 3 of these substituents at the substitutable position, and when the number of the substituent is two or more, the substituent may be the same or different.

More specifically, the group represented by the formula:

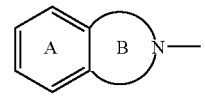

wherein the symbols are as defined above, includes groups represented by the formulas:

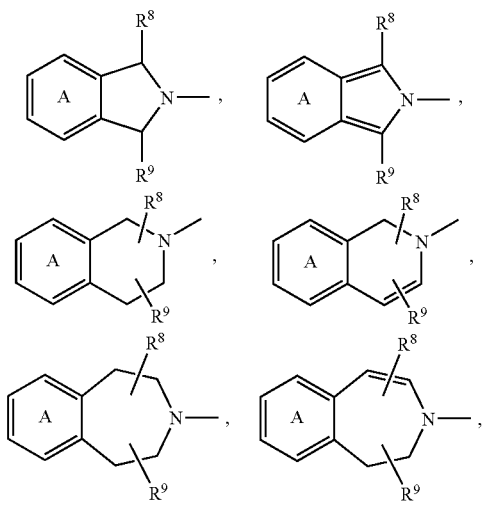

-continued

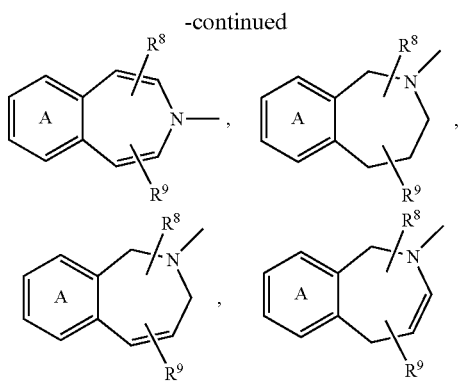

wherein R⁸ and R⁹ are the same or different and each is a hydrogen atom, a halogen or an optionally substituted hydrocarbon group, and the ring A is as defined above, and the like, preferably the groups represented by the formulas:

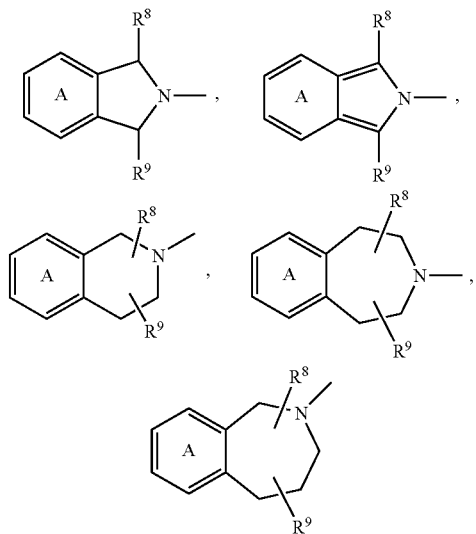

wherein the symbols are as defined above, and the like, and more preferably the groups represented by the formulas:

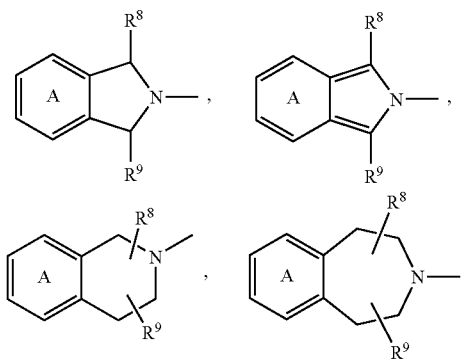

wherein the symbols are as defined above, and the like. Of these, the groups represented by the formula:

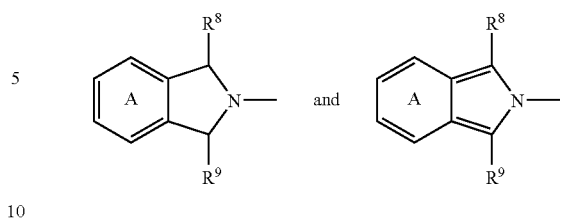

wherein the symbols are as defined above, and the like are specifically preferred.

The "halogen" or "optionally substituted hydrocarbon group" represented by $R^8$ and $R^9$ includes those exemplified by the "halogen" or "optionally substituted hydrocarbon group" as the "substituent" of the above-mentioned ring B.

The "leaving group" represented by $L^1$ and $L^2$ includes for example a hydroxy, a halogen atom (e.g., fluorine, chlorine, bromine, iodine and the like), an optionally halogenated $C_{1-5}$ alkylsulfonyloxy (e.g., methanesulfonyloxy, ethanesulfonyloxy, trichloromethanesulfonyloxy and the like), an optionally substituted $C_{6-10}$ arylsulfonyloxy and the like. The "optionally substituted $C_{6-10}$ arylsulfonyloxy" includes a $C_{6-10}$arylsulfonyloxy (e.g., phenylsulfonyloxy, naphthylsulfonyloxy and the like) optionally having 1 to 3 substituents selected from a $C_{1-6}$ alkyl (e.g., methyl, ethyl, propyl, isopropyl, butyl, isobutyl, sec-butyl, tert-butyl, pentyl, hexyl and the like), a $C_{1-6}$alkoxy (e.g., methoxy, ethoxy, propoxy, isopropoxy, butoxy, isobutoxy, sec-butoxy, pentyloxy, hexyloxy and the like) and a nitro. Specific examples thereof include benzenesulfonyloxy, m-nitrobenzenesulfonyloxy, p-toluenesulfonyloxy and the like.

The compound (III) is a compound which may form the ring represented by A and B of the compound (IV) together with the nitrogen atom of the amino group substituted on the ring C of the compound (I").

The amount of the compound (III) to be used is about 0.8 to about 5.0 mol, preferably about 1.0 to about 2.0 mol relative to 1 mol of the compound (I").

The "base" includes basic salts such as sodium carbonate, potassium carbonate, cesium carbonate, sodium hydrogencarbonate and the like, aromatic amines such as pyridine, lutidine and the like, tertially amines such as triethylamine, tripropylamine, tributylamine, cyclohexyldimethylamine, 4-dimethylaminopyridine, N,N-dimethylaniline, N-methylpiperidine, N-methylpyrrolidine, N-methyl morpholine and the like, alkaline metal hydrides such as sodium hydride, potassium hydride and the like, metal amides such as sodium amide, lithium diisopropylamide, lithium hexamethyl disilazide and the like, metal alkoxides such as sodium methoxide, sodium ethoxide, potassium tert-butoxide and the like.

The amount of the base to be used is about 0.5 to about 10.0 mol, preferably about 1.0 to about 3.0 mol relative to 1 mol of the compound (I"). Furthermore, if necessary, the production can be carried out by reacting with the base under the co-existence of a quaternary ammonium salt.

The "quaternary ammonium salt" includes for example tetrabutylammonium iodide and the like.

The amount of the quaternary ammonium salt to be used is about 0.1 to about 3.0 mol, preferably about 0.5 to about 1.0 mol relative to 1 mol of the compound (I").

It is advantageous to carry out the present reaction using an inert solvent. Such solvent is not specifically limited as long as the reaction exceeds, and includes, for example, alcohols such as methanol, ethanol, propanol, butanol and the like, ethers such as diethylether, tetrahydrofuran, dioxane, 1,2- dimethoxyethane and the like, hydrocarbons such as benzene, toluene, cyclohexane, hexane and the like, amides such as N,N-dimethylformamide, N,N-dimethylacetamide and the like, halogenated hydrocarbons such as dichloromethane, chloroform, carbon tetrachloride, 1,2-dichloroethane and the like, nitrites such as acetonitrile, propionitrile and the like, sulfoxides such as dimethylsulfoxide and the like, or a mixed solvent thereof and the like, are preferred.

The reaction period is generally about 30 min to about 72 hr, preferably about 3 hr to about 24 hr. The reaction temperature is generally about −20 to about 200° C., preferably about 20 to about 150° C.

Examples of the compound (IV) include (R)—(+)-5,6-dimethoxy-2-[2,2,4,6,7-pentamethyl-3-(4-methylphenyl)-2,3-dihydro-1-benzofuran-5-yl]isoindoline, (R)—(+)-5,6-dimethoxy-2-[2,2,4,6,7-pentamethyl-3-(1-methylethylphenyl)-2,3-dihydro-1-benzofuran-5-yl] isoindoline, (R)—(+)-5,6-dimethoxy-2-[2,2,4,6,7-pentamethyl-3-(4-bromophenyl)-2,3-dihydro-1-benzofuran-5-yl]isoindoline or a salt thereof.

The salt of the compound (IV) may be, when the compound (IV) has an acidic group such as —COOH and the like, for example, a metal salt, an ammonium salt, a salt with an organic base and the like, or when the compound (IV) has a basic group such as —$NH_2$ and the like, for example, a salt with an inorganic acid, an organic acid, or a basic or acidic amino acid or the like, or an intramolecular salt. Preferred examples of the metal salt include for example alkaline metal salts such as sodium salt, potassium salt and the like; alkaline earth metal salts such as calcium salt, magnesium salt, barium salt and the like; aluminum salt and the like. Preferred examples of the salt with an organic base include for example a salt with trimethylamine, triethylamine, pyridine, picoline, ethanolamine, diethanolamine, triethanolamine, dicyclohexylamine, N,N-dibenzylethylenediamine or the like. Preferred examples of the salt with an inorganic acid include for example a salt with hydrochloric acid, hydrobromic acid, nitric acid, sulfuric acid, phosphoric acid or the like. Preferred examples of the salt with an organic acid include for example a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid or the like. Preferred examples of the salt with a basic amino acid includes for example a salt with arginine, lysine, ornithine or the like, and preferred examples of the salt with an acidic amino acid includes for example a salt with aspartic acid, glutamic acid or the like.

Of these, a pharmaceutically acceptable salt is preferred. For example, when the compound has an acidic functional group, inorganic salts such as alkaline metal salts (e.g., a sodium salt, a potassium salt and the like), alkaline earth metal salts (e.g., a calcium salt, a magnesium salt, a barium salt and the like) and the like, ammonium salts and the like are exemplified. Alternatively, when the compound has a basic functional group, inorganic salts such as hydrochloride, sulfate, phosphate, hydrobromide and the like, and organic salts such as acetate, maleate, fumarate, succinate, methanesulfonate, p-toluenesulfonate, citrate, tartarate and the like, are exemplified.

The compound (IV) acts as a neurotrophic factor-like substance, a neurotrophic factor activity-enhancing substance or a nerve degeneration-suppressing substance, or a β amyloid toxicity-suppressing substance and the like, to mammals (e.g., mouse, rat, hamster, rabbit, cat, dog, cattle, sheep, monkey, human and the like), and suppresses nerve cell death and accelerates nerve regeneration. Furthermore, the compound of the present invention has activation action for cholinergic system (e.g., activity-enhancing action for cholineacetyltransferase and the like), and increases the content of acetylcholine and activates nerve function and the like.

Therefore, the compound (IV) is useful for, for example, nerve degenerative diseases (e.g., Alzheimer's disease, Parkinson's disease, amyotrophic lateral sclerosis (ALS), Huntington's disease, spinocerebellar degeneration and the like), psychoneurosis (e.g., schizophrenia and the like), head trauma, spinal injury, cerebrovascular disorder, cerebrovascular dementia, peripheral nerve disorder (e.g., diabetic nerve disorder and the like) and the like. The compound (IV) is used for an agent for prevention or treatment of these diseases.

The usage such as preparation for prevention or treatment of these diseases, administration route, dosage form and the like, can follow those disclosed in WO00/34262.

Namely, the compound (IV) has low toxicity, and can be safely administered orally or parenterally (e.g., local, rectal, intravenous and the like) as it is, or as a pharmaceutical composition such as tablet (including sugar-coated tablet, film-coated tablet, buccal disintegrating tablet and the like), powder, granule, capsule (including soft capsule), liquid, injection, suppository, sustained-release agent, adhesive and the like, which is produced by mixing with a pharmacologically acceptable carrier according to a mean known per se.

The content of the compound (IV) in the preparation of the present invention is about 0.01 to about 100 wt % relative to whole preparation.

The dose varies depending on the object of administration, administration route, disease and the like, and when the compound is administered to an adult as an oral therapeutic agent for Alzheimer's disease, the amount of the compound of the present invention as an active ingredient is about 0.1 to about 20 mg/kg body weight, preferably about 0.2 to about 10 mg/kg body weight, more preferably about 0.5 to about 10 mg/kg body weight, and the agent can be administered in a portion or portions per a day.

Furthermore, the compound may be used in combination with the other active ingredients [e.g., choline esterase inhibitors (e.g., Aricept (Donepezil) and the like), cerebral activators (e.g., Vinpocetine and the like), medicaments for treating Parkinson's disease (e.g., L-Dopa, Deprenyl and the like), medicaments for treating amyotrophic lateral sclerosis (Riluzole and the like), neurotrophic factors and the like]. The other active ingredients and the compound of the present invention or a salt thereof can be used in combination by mixing according to a method known per se and formulating the mixture in one pharmaceutical composition (e.g., tablet, powder, granule, capsule (including soft capsule), liquid, injection, suppository, sustained-release agent and the like). The ingredient and the compound may be formulated independently, and may be administered to the same object simultaneously or at intervals. Alternatively, the compound may be used in combination with a drug such as an immunosuppressive agent and the like during or after implantation of nerve stem cell and pre-nerve cell that have been prepared from embryonic stem cell and nerve tissue or fetal nerve tissue.

The pharmacologically acceptable carrier that may be used in the production of the preparation includes various organic or inorganic carrier substances conventionally used as a preparation material, such as excipients, lubricating agents, binders, disintegrators for solid preparations; solvents, dissolution aids, suspending agents, isotonic agents, buffers, soothing agents for liquid preparations, and the like. Furthermore, if necessary, additives such as conventional preservatives, antioxidants, coloring agents, sweetening agents, absorbents, wetting agents and the like can be used.

The excipients include for example lactose, sucrose, D-mannitol, starch, corn starch, crystalline cellulose, light anhydrous silicic acid and the like.

The lubricating agents include for example magnesium stearate, calcium stearate, talc, colloidal silica and the like.

The binders include for example crystalline cellulose, sucrose, D-mannitol, dextrin, hydroxypropylcellulose, hydroxypropylmethylcellulose, polyvinylpyrrolidone, starch, saccharose, geratin, methylcellulose, carboxymethylcellulose sodium and the like.

The disintegrators include for example starch, carboxymethylcellulose, carboxymethylcellulose calcium, croscarmelose sodium, carboxymethyl starch sodium, L-hydroxypropylcellulose and the like.

The solvents include for example water for injection, alcohol, propylene glycol, macrogol, sesame oil, corn oil, olive oil and the like.

The dissolution aids include for example polyethylene glycol, propylene glycol, D-mannitol, benzyl benzoate, ethanol, trisaminomethane, cholesterol, triethanolamine, sodium carbonate, sodium citrate and the like.

The suspending agents include for example surfactants such as triethanolamine stearate, sodium lauryl sulfate, laurylaminopropionic acid, lecithin, benzalkonium chloride, benzethonium chloride, glycerine monostearate and the like; hydrophilic polymers such as polyvinylalcohol, polyvinylpyrrolidone, carboxymethylcellulose sodium, methylcellulose, hydroxymethylcellulose, hydroxyethylcellulose, hydroxypropylcellulose and the like.

The isotonic agents include for example glucose, D-sorbitol, sodium chloride, glycerine, D-mannitol and the like.

The buffers include for example buffer solutions such as phosphorate, acetate, carbonate, citrate and the like, and the like.

The soothing agents include for example benzylalcohol and the like.

The preservatives include for example paraoxy benzoates, chlorobutanol, benzylalcohol, phenethylalcohol, dehydroacetic acid, sorbic acid and the like.

The antioxidants include for example sulfite, ascorbic acid, α-tocopherol and the like.

EXAMPLES

Hereinafter the present invention is explained in more detail with referring to Examples and Reference Examples, which do not limit the present invention.

Nuclear magnetic resonance ($^1$H-NMR) was measured using tetramethylsilane as an internal standard and using JMTCO400/54 (400 MHz, manufactured by JEOL Co., Ltd.) or R-90H (90 MHz, manufactured by Hitachi Ltd.), and the δ value was represented by ppm. The symbols in the Examples are as follows.

s: singlet, d: doublet, t: triplet, m: multiplet, br: broad, J: coupling constant The excess percentage of enantiomer (% ee) and excess percentage of diastereomer (% de) were measured by high performance liquid chromatography using a column for the separation of optical isomers.

High performance liquid chromatography condition A
Column; CHIRALCEL OD (manufactured by Daicel Chemical Industries, Ltd.)
Eluent; n-hexane/isopropanol (97/3)
Flow rate; 0.5 ml/min.
Detection; UV 230 nm
Temperature; room temperature High performance liquid chromatography condition B
Column; SUMICHIRAL OA-3300 4.6×250 mm (manufactured by Sumika Chemical Analysis Service)
Mobile phase; 0.05 M acetic acid-ammonium-ethanol solution
Flow rate; 0.3 ml/min
Detection; UV (254 nm)
Temperature; room temperature Example 1

Preparation of (R)—(+)-2,2,4,6,7-pentamethyl-3-(4-methylphenyl)-2,3-dihydro-1-benzofuran-5-amine (2S,3S)-(+)—O,O'-Di-(p-toluoyl)tartaric acid (1936 g) was dissolved in isopropylalcohol (14.8 L) at 75° C. A solution of a racemate of 2,2,4,6,7-pentamethyl-3-(4-methylphenyl)-2,3-dihydro-1-benzofuran-5-amine (1850 g) in toluene (9244 ml) was then added dropwise thereto and the mixture was stirred at the same temperature for 10 min. The mixture was stirred at 67 to 69° C. for 30 min and cooled to room temperature (25 to 30° C.), and the precipitated crystals were collected by filtration, washed with toluene/isopropylalcohol (5:1) to give a diastereomeric salt (2234 g).

Melting point 193-194° C., $[\alpha]_D^{25}$=+79.2° (c=1.0, MeOH)
$^1$H-NMR (DMSO-d$_6$) δ: 0.88 (3H, s), 1.37 (3H, s), 1.67 (3H, s), 2.01 (3H, s), 2.05 (3H, s), 2.24 (3H, s), 2.39 (6H, s), 4.08 (1H, s), 5.80 (2H, s), 6.60-7.10 (4H, br), 7.27 (4H, d, J=8.0 Hz), 7.89 (4H, d, J=8.0 Hz)

The above-mentioned diastereomeric salt was dissolved in methanol (12.025 L) at 45° C., and 25% aqueous ammonium was added dropwise thereto to adjust the pH to 8.5. The mixture was stirred at 50° C. for 10 min. Water (3105 ml) was added thereto, and after the crystals began to precipitate, additional water (4163 ml) was added thereto. The mixture was stirred at 50° C. for 1 hr, then at 25 to 30° C. for 1 hr, and the crystals were collected by filtration and washed with 50% methanol to give the title compound (805.1 g). Yield 87%.

Melting point 91-92° C., $[\alpha]_D^{25}$=+5.2° (c=1.0, MeOH)
$^1$H-NMR (CDCl$_3$) δ: 1.01 (3H, s), 1.48 (3H, s), 1.79 (3H, s), 2.14 (3H, s), 2.20 (3H, s), 2.31 (3H, s), 3.08 (2H, br), 4.10 (1H, s), 6.60-7.10 (4H, br)

Example 2

Preparation of (R)—(+)-2,2,4,6,7-pentamethyl-3-(4-methylphenyl)-2,3-dihydro-1-benzofuran-5-amine (2S,3S)-(+)-O,O'-Di-(p-toluoyl)tartaric acid (78.5 g) was dissolved in 2-propanol (288 ml). A racemate of 2,2,4,6,7-pentamethyl-3-(4-methylphenyl)-2,3-dihydro-1-benzofuran-5-amine (60 g) and acetonitrile (960 ml) were added thereto, and the mixture was stirred at room temperature for 8 hr. The precipitate was filtered off to give crude crystals. The crystals were suspended in acetonitrile (600 ml), stirred overnight under room temperature and filtered. The obtained crystals were 54.9 g. Yield 40%. As a result of HPLC analysis, the excess percentage of the diastereomer was 99% de.

Melting point 186-187° C., $[\alpha]_D^{25}$=+79.9 (c=1.0, MeOH)
$^1$H-NMR (DMSO-d$_6$) δ; 0.89 (3H, s), 1.37 (3H, s), 1.67 (3H, s), 2.00 (3H, s), 2.05 (3H, s), 2.25 (3H, s), 2.40 (6H, s), 4.09 (1H, s), 5.80 (2H, s), 6.60-7.10 (4H, br), 7.39 (4H, d, J=7.8 Hz), 7.89 (4H, d, J=8.0 Hz)

This diastereomeric salt was decomposed in saturated aqueous sodium hydrogencarbonate (550 ml) and ethyl acetate (550 ml) to give the title compound (23.2 g, yield 78%). As a result of HPLC analysis, the excess percentage of the enantiomer was 99% ee.

Melting point 90-91° C., $[\alpha]_D^{25}$=+5.1 (c=1.0, MeOH) $^1$H-NMR (CDCl$_3$) δ: 1.00 (3H, s), 1.46 (3H, s), 1.77 (3H, s), 2.12 (3H, s), 2.19 (3H, s), 2.30 (3H, s), 3.23 (1H, br), 4.08 (1H, s), 6.60-7.10 (4H, br)

Example 3

Preparation of (R)—(+)-2,2,4,6,7-pentamethyl-3-(4-methylphenyl)-2,3-dihydro-1-benzofuran-5-amine (2S,3S)-(+)-O,O'-Di-(p-toluoyl)tartaric acid (99.3 g) was dissolved in 2-propanol (374 ml). A racemate of 2,2,4,6,7-pentamethyl-3-(4-methylphenyl)-2,3-dihydro-1-benzofuran-5-amine (80 g) and acetonitrile (1280 ml) were added thereto and the mixture was stirred at room temperature for 8 hr. The precipitate was filtered off to give crude crystals (97% de). The crystals were suspended in acetonitrile (800 ml) and stirred overnight under room temperature, and the mixture was filtered. The obtained crystals were 71.7 g. As a result of HPLC analysis, the excess percentage of the diastereomer was 99% de.

The diastereomeric salt was decomposed in saturated aqueous sodium hydrogencarbonate (720 ml) and ethyl acetate (720 ml) to give the title compound (30.7 g, yield 76%). As a result of HPLC analysis, the excess percentage of the enantiomer was 99% ee.

Example 4

Preparation of (+)-2,2,4,6,7-pentamethyl-3-[4-(1-methylethyl) phenyl]-2,3-dihydro-1-benzofuran-5-amine A racemate of 2,2,4,6,7-pentamethyl-3-[4-(1-methylethyl) phenyl]-2,3-dihydro-1-benzofuran-5-amine (50 mg) and (S)—(+)-N-(3,5-dinitrobenzoyl)-α-phenylglycine (53.3 mg) were dissolved in 2-propanol (1 ml) with heating, and the mixture was left in a refrigerator for 20 hr. The precipitated salt was collected by filtration and washed with 2-propanol (0.3 ml) to give colorless crystals (68.1 mg). The crystals were recrystallized from 2-propanol (1 ml then 0.6 ml) to give 35.3 mg. (Yield 42.5%) (In the crystals, the resolved substance and the resolution agent were crystallized in the ratio of 1:2, and the crystals further contained 1 mol of 2-propanol.) As a result of HPLC analysis, the excess percentage of the diastereomer was >99.9% de.

Melting point 183-185° C. (the crystal form was changed at 120-125° C.), $[\alpha]_D^{25}$=+50.6° (c=0.52, MeOH) $^1$H-NMR (CDCl$_3$) δ: 0.88 (3H, s), 1.03 (3H, s), 1.05 (3H, s), 1.16 (3H, s), 1.18 (3H, s), 1.37 (3H, s), 1.65 (3H, s), 1.99 (3H, s), 2.05 (3H, s), 2.83 (1H, m), 3.77 (1H, m), 4.07 (1H, s), 4.32 (1H, d, J=4.2 Hz), 5.64 (2H, d, J=7.1 Hz), 7.11 (2H, d, J=8.1 Hz), 7.36-7.53 (10H, m), 8.97 (2H, m), 9.13 (4H, d, J=2.2 Hz), 9.87 (2H, d, J=6.8 Hz)

The above-mentioned salt (31 mg) was stirred with aqueous 5% sodium hydrogencarbonate (1 ml) and ethyl acetate (2 ml) for 10 min. The organic layer was separated and concentrated to give the title compound as a colorless oil (10.4 mg). (Crude yield 47.2%) As a result of HPLC analysis, the excess percentage of enantiomer of the (+) form having short retention time was >99.9% ee.

Example 5

Preparation of (+)-2,2,4,6,7-pentamethyl-3-[4-(1-methylethyl) phenyl]-2,3-dihydro-1-benzofuran-5-amine A racemate of 2,2,4,6,7-pentamethyl-3-[4-(1-methylethyl) phenyl]-2,3-dihydro-1-benzofuran-5-amine (100 mg) and (S)-(+)-N-(3,5-dinitrobenzoyl)-α-phenylglycine (213.2 mg) were dissolved in 2-propanol (4 ml) with heating, and the solution was left in a refrigerator for 20 hr. The precipitated salt was collected by filtration and washed with 2-propanol (1 ml) to give colorless crystals (228 mg). The crystals were recrystallized from 2-propanol (4 ml) twice to give crystals (104 mg, yield 62.6%). (In the crystals, the resolved substance and the resolution agent were crystallized in the ratio of 1:2, and the crystals further contained 1 mol of 2-propanol.) As a result of HPLC analysis, the excess percentage of the diastereomer was >99.9% de.

Melting point 184.5-185.5° C. (the crystal form was changed at 123-125° C.) Elemental analysis (for $C_{55}H_{59}N_7O_{16}$) Calcd. for C, 61.50%; H, 5.54%; N, 9.13%; Found. C, 60.63%; H, 5.33%; N, 9.13%.
$^1$H-NMR (CDCl$_3$) δ: 0.88 (3H, s), 1.03 (3H, s), 1.05 (3H, s), 1.16 (3H, s), 1.18 (3H, s), 1.37 (3H, s), 1.65 (3H, s), 1.99 (3H, s), 2.05 (3H, s), 2.83 (1H, m), 3.77 (1H, m), 4.07 (1H, s), 4.32 (1H, d, J=4.2 Hz), 5.64 (2H, d, J=7.1 Hz), 7.11 (2H, d, J=8.1 Hz), 7.36-7.53 (10H, m), 8.97 (2H, m), 9.13 (4H, d, J=2.2 Hz), 9.87 (2H, d, J=6.8 Hz)

The above-mentioned salt (86 mg) was stirred with 5% aqueous sodium hydrogencarbonate (3 ml) and ethyl acetate (5 ml) for 10 min. The organic layer was separated, concentrated and purified by silica gel column chromatography (chloroform/methanol=30/1) to give the title compound as a colorless oil (21 mg, yield 50.8%). This oil was crystallized by leaving it under room temperature. As a result of HPLC analysis, the excess percentage of the enantiomer for the (+) form having short retention time was >99.9% ee.

Melting point 75-76° C., $[\alpha]_D^{22}$=+5.2° (c=0.39, MeOH) 1H-NMR (CDCl$_3$) δ: 1.00 (3H, s), 1.20 (3H, s), 1.22 (3H, s), 1.47 (3H, s), 1.78 (3H, s), 2.12 (3H, s), 2.19 (3H, s), 2.85 (1H, m), 3.24 (2H, bs), 4.08 (1H, s),6.87 (2H, br), 7.06-7.08 (2H, m)

Example 6

Preparation of (+)-2,2,4,6,7-pentamethyl-3-[4-(1-methylethyl)phenyl]-2,3-dihydro-1-benzofuran-5-amine A racemate of 2,2,4,6,7-pentamethyl-3-[4-(1-methylethyl) phenyl]-2,3-dihydro-1-benzofuran-5-amine (50 mg) and (2S,3S)-(+)-O,O'-di-(p-toluoyl)tartaric acid (59.7 mg) were dissolved in 2-propanol (0.6 ml) and toluene (0.4 ml), and the solution was left in a refrigerator for 20 hr. The precipitated crystals were collected by filtration to give a salt (48.2 mg). The salt was recrystallized from 2-propanol (0.4 ml) and toluene (0.25 ml) to give crystals (32 mg, yield 58.3%). As a result of HPLC analysis, the excess percentage of diastereomer was >99.9% de.

Melting point 185-186° C.
$^1$H-NMR (CDCl$_3$) δ: 0.89 (3H, s), 1.16 (3H, s), 1.18 (3H, s), 1.38 (3H, s), 1.67 (3H, s), 2.01 (3H, s), 2.05 (3H, s), 2.41 (6H, s), 2.83 (1H, m), 4.09 (1H, s),5.81 (2H, s), 7.12 (2H, d, J=8.1 Hz), 7.40 (4H, d, J=8.1 Hz), 7.89 (4H, d, J=8.3 Hz)

The above-mentioned salt (30 mg) was stirred with 5% aqueous sodium hydrogencarbonate (1 ml) and ethyl acetate (1 ml) for 10 min. The organic layer was separated and concentrated to give the title compound as a colorless oil (12.3 mg, yield 52.5%). As a result of HPLC analysis, the excess percentage of the enantiomer for the (+) form having short retention time was>99.9% ee.

Example 7

Preparation of (+)-2,2,4,6,7-pentamethyl-3-[4-(1-methylethyl)phenyl]-2,3-dihydro-1-benzofuran-5-amine A racemate of 2,2,4,6,7-pentamethyl-3-[4-(1-methylethyl)phenyl]-2,3-dihydro-1-benzofuran-5-amine (50 mg) and (+)-2-hydroxy-5,5-dimethyl-4-(1-naphthyl)-1,3,2-dioxaphosphorinane 2-oxide (44.9 mg) were dissolved in 2-propanol (0.4 ml) and t-butylmethylether (1 ml), and the solution was left in a refrigerator for 20 hr. The precipitated crystals were collected by filtration to give a salt (39.2 mg). This was stirred in 2-propanol (0.4 ml) and diisopropylether (1 ml) with heating, left at room temperature for 18 hr, and filtered. Colorless crystals were obtained (18.5 mg, yield 39.0%). As a result of HPLC analysis, the excess percentage of the diastereomer was>99.9% de.

Melting point; 220-221° C. $^1$H-NMR (CDCl$_3$) δ: 0.61 (3H, s), 0.90 (3H, s), 1.01 (3H, s), 1.16 (3H, s), 1.18 (3H, s), 1.38 (3H, s), 1.71 (3H, s), 2.05 (3H, s), 2.07 (3H, s), 2.83 (1H, m), 3.84 (1H, dd, J=11.0 Hz, 24.6 Hz), 4.11 (1H, s), 4.42 (1H, d, J=11.0 Hz), 6.15 (1H, s), 7.12 (2H, d, J=7.1 Hz), 7.49-7.59 (4H, m), 7.92 (2H, m), 8.26 (1H, d, J=8.8 Hz)

Example 8

Preparation of 3-(4-bromophenyl)-2,2,4,6,7-tetramethyl-2,3-dihydrobenzofuran-5-amine (2S,3S)-(+)-O,O'-Di-(p-toluoyl)tartaric acid (3.86 g) was dissolved in isopropylalcohol (14.2 ml) at 70° C., and a solution of 2-(4-bromophenyl)-2,2,4,6,7-tetramethyl-2,3-dihydrobenzofuran-5-amine (3.60 g) in acetonitrile (47.5 ml) was added dropwise thereto while keeping the internal temperature at 60° C. The mixture was cooled to 30° C. for about 3 hr, and stirred for 2 hr at the same temperature. The precipitated crystals were collected by filtration and washed with a small amount of cooled acetonitrile. The obtained crude diastereomeric salt was suspended in acetonitrile (29.6 ml) and stirred overnight. The crystals were collected by filtration, washed with a small amount of cooled acetonitrile and dried under reduced pressure. The crystals were suspended in ethyl acetate (100 ml). Saturated aqueous sodium hydrogencarbonate (100 ml) was added thereto, and the mixture was stirred thoroughly and partitioned. The organic layer was washed successively with water (100 ml) and saturated brine (100 ml), and dried over anhydrous sodium sulfate. The solvent was distilled off under reduced pressure, and the residue was crystallized from cooled hexane to give the title compound (1.13 g, yield 31.4%). As a result of HPLC analysis, the excess percentage of the enantiomer for the (+) form having short retention time was>99.9% ee.

Melting point 143-144° C., $[\alpha]_D^{20}$=+11.60° (c=0.507, MeOH) $^1$H-NMR (CDCl$_3$) δ: 1.00 (3H, s), 1.47 (3H, s), 1.77 (3H, s), 2.12 (3H, s), 2.18 (3H, s), 3.25 (2H, br), 4.07 (1H, s), 6.85 (2H, br), 7.36 (2H, br, J=6.9 Hz).

Reference Example 1

Preparation of ethyl 2-methyl-3-(4-methylphenyl)-2-propenoate

To dimethylformamide (1802 ml) that had been cooled to −10° C. was added sodium tert-butoxide (528.6 g) and the solution was stirred at −5 to 0° C. for 30 min. Triethyl 2-phosphonopropionate (1310 g) was added dropwise thereto at 10° C. or below. The solution was stirred at 2 to 5° C. for 1 hr, and 4-methylbenzaldehyde (600.8 g) was added dropwise thereto at 10° C. or below and the solution was stirred at room temperature for 1 hr. Water was added thereto and the solution was extracted with toluene. The extract was washed with water and the solvent was distilled off to give the title compound as an oil (1009 g, yield 98.8%).

$^1$H-NMR (CDCl$_3$) δ: 1.35 (3H, t, J=7.1 Hz), 2.12 (1H, s), 2.37 (3H, s), 4.27 (2H, q, J=7.1 Hz), 7.13-7.32 (4H, m), 7.66 (1H, s)

Reference Example 2

Preparation of 2-methyl-3-(4-methylphenyl)-2-propen-1-ol

To a solution of ethyl 2-methyl-3-(4-methylphenyl)-2-propenoate (1002 g) in toluene (5371 ml) was added dropwise a 70% solution of dihydrobis(2-methoxyethoxy) sodium aluminate in toluene (2152 g) at 10° C. or below. The solution was stirred at 2 to 5° C. for 1 hr, a 10% solution of Rochel's salt (5968 ml) was added dropwise thereto at 20° C. or below and the solution was stirred at room temperature for 30 min. The toluene layer was fractionated, and washed with a 10% solution of Rochel's salt (2984 ml) and then washed with water. The solvent was distilled off to give the title compound as an oil (756 g, yield 93.9%).

$^1$H-NMR (CDCl$_3$) δ: 1.90 (3H, s), 2.34 (3H, s), 4.13 (2H, s), 6.50 (1H, s), 7.06-7.20 (4H, m)

Reference Example 3

Preparation of 1-(3-chloro-2-methyl-1-propenyl)-4-methylbenzene

To a solution of 2-methyl-3-(4-methylphenyl)-2-propen-1-ol (750 g) in toluene (2367 ml) was added dimethylformamide (29.6 ml). To the solution was added dropwise thionyl chloride (431.1 ml) at 20° C. or below and the solution was stirred at 12 to 15° C. for 1.5 hr. Water was then added thereto under ice-cooling. The toluene layer was fractionated and a 10% aqueous solution of sodium carbonate was added thereto to adjust the pH to 5. The toluene layer was fractionated again, washed successively with 5% sodium hydrogencarbonate and 5% brine. The solvent was distilled off to give the title compound as an oil (776.8 g, yield 87.3%).

$^1$H-NMR (CDCl$_3$) δ: 1.98 (3H, s), 2.35 (3H, s), 4.21 (2H, s), 6.55 (1H, s), 7.13-7.20 (4H, m)

Reference Example 4

Preparation of N-[2,3,6-trimethyl-4-[[2-methyl-3-(4-methylphenyl)-2-propenyl]oxy]phenyl]formamide To a mixture of N-(4-hydroxy-2,3,6-trimethylphenyl)formamide (660.4 g), potassium carbonate (1019 g) and dimethylformamide (3302 ml) was added a solution of 1-(3-chloro-2-methyl-1-propenyl)-4-methylbenzene (755 g) in toluene (675 ml), and the mixture was stirred at 50° C. for 14 hr. Water (5944 ml) was then added thereto and the mixture was stirred at 30° C. for 1 hr. The precipitated crystals were collected by filtration and washed with water and isopropylether to give the title compound (940 g, yield 74.5%).

$^1$H-NMR (CDCl$_3$) δ: 1.98 (3H, s), 2.07-2.38 (9H, m), 2.35 (3H, s), 4.53 (2H, d, J=6.6 Hz), 6.61 (1H, s), 6.82-7.09 (1H, m), 7.11-7.31 (4H, m), 7.98 (0.5H, d, J=12.2 Hz), 8.38 (0.5H, s)

Reference Example 5

Preparation of N-[4-hydroxy-3-[2-methyl-1-(4-methylphenyl)-1-propenyl]-2,5,6-trimethylphenyl]formamide A mixture of N-[2,3,6-trimethyl-4-[[2-methyl-3-(4-methylphenyl)-2-propenyl]oxy]phenyl]formamide (920 g), potassium carbonate (4.6 g) and N,N-dimethylaniline (2760 ml) was stirred at 190° C. for 4 hr under nitrogen stream. The mixture was cooled to 100° C. and heptane (1840 ml) was added dropwise thereto. The mixture was further cooled to 30° C. and heptane (3680 ml) was added dropwise thereto. The mixture was stirred at the same temperature for 1 hr, and the precipitated crystals were collected by filtration and washed with heptane to give the title compound (799.5 g, yield 86.9%).

$^1$NMR (DMSO-d$_6$) δ: 1.51 (3H, s), 1.85 (3H, s), 1.89 (3H, s), 1.94-2.10 (6H, m), 2.24 (3H, s), 7.05 (4H, s), 7.70 (1H, br), 7.77-8.18 (1H, m), 8.96-9.15 (1H, m)

Reference Example 6

Preparation of 2,2,4,6,7-pentamethyl-3-(4-methylphenyl)-2,3-dihydro-1-benzofuran-5-amine To a mixture of N-[4-hydroxy-3-[2-methyl-1-(4-methylphenyl)-1-propenyl]-2,5,6-trimethylphenyl]formamide (740 g) and isobutanol (2220 ml) was added concentrated hydrochloric acid (2220 ml) under nitrogen stream and the mixture was refluxed under heating for 5 hr. The mixture was stirred at 0 to 5° C. for 1 hr. The crystals were collected by filtration and washed with toluene to give 2,2,4,6,7-pentamethyl-3-(4-methylphenyl)-2,3-dihydro-1-benzofuran-5-amine hydrochloride. This hydrochloride was dissolved in a mixed solution of methanol (5180 ml)/water (740 ml) at 55 to 60° C. To the solution was added dropwise 25% aqueous ammonium at 50° C. to adjust the pH to 8.5, and the mixture was stirred for 30 min. The precipitated crystals were collected by filtration and washed with methanol/water (1:1) to give the title compound (587.2 g, yield 87.4%).

$^1$H-NMR (CDCl$_3$) δ: 0.99 (3H, s), 1.47 (3H, s), 1.77 (3H, s), 2.12 (3H, s), 2.19 (3H, s), 2.30 (3H, s), 3.23 (2H, br), 4.08 (1H, s), 6.60-7.23 (4H, m)

Reference Example 7

Preparation of (R)—(+)-5,6-dimethoxy-2-(2,2,4,6,7-pentamethyl-3-(4-methylphenyl)-2,3-dihydro-1-benzofuran-5-yl)isoindoline To a solution of 1,2-bischloromethylveratrol (675.9 g) in toluene (4000 ml) was added dropwise a solution of (+)-2,2,4,6,7-pentamethyl-3-(4-methylphenyl)-2,3-dihydro-1-benzofuran-5-amine (800 g) and N-ethyldiisopropylamine (943.2 g) in toluene (3867 ml) under nitrogen stream, with heating at the inner temperature of 100° C. for 4.5 hr. After dropping, the mixture was further stirred at 100° C. for 1 hr. The mixture was cooled to the inner temperature of 45° C., methanol (1040 ml) was added thereto and concentrated hydrochloric acid (333.6 ml) was added dropwise thereto. After the crystals were precipitated, the mixture was stirred at 50° C. for 30 min and stirred at 5° C. for 1 hr. The crystals were collected by filtration, and washed with toluene and 50% ethanol to give (R)—(+)-5,6-dimethoxy-2-(2,2,4,6,7-pentamethyl-3-(4-methylphenyl)-2,3-dihydro-1-benzofuran-5-yl) isoindoline hydrochloride (1119 g, 83.6%). This hydrochloride was dissolved in a mixed solution of 90% ethanol (5600 ml) and concentrated hydrochloric acid (110 ml), and 2,6-di-tert-butyl-4-hydroxytoluene (8.0 g) was added thereto. To the solution was added dropwise 6.25% aqueous ammonium at 50° C. to adjust the pH to 8.0, and water (640 ml) was added thereto. The mixture was stirred at 50° C. for 30 min and stirred at room temperature for 1 hr. The precipitated crystals were collected by filtration, washed with 70% ethanol to give the title compound (935 g, yield 75.5%).

Melting point 157-159° C., [α]$_D$=+62.3° (c=0.488, MeOH) $^1$H-NMR (CDCl$_3$) δ: 1.01 (3H, s), 1.48 (3H, s), 1.76 (3H, s), 2.17 (3H, s), 2.18 (3H, s), 2.30 (3H, s), 3.87 (6H, s), 4.09 (1H, s), 4.45 (4H, s), 6.76-7.06 (6H, m)

Reference Example 8

2-Hydroxy-5,5-dimethyl-4-(1-naphthyl)-1,3,2-dioxaphosphorinane 2-oxide 1) 2,2-Dimethyl-1-(1-naphthyl)-1,3-propanediol 1-Naphthoaldehyde (57.72 g, 0.37 mol) and isobutylaldehyde (55.0 g, 0.76 mol) was mixed and 85% potassium hydroxide (24.5 g, 0.37 mol) dissolved in ethanol (340 ml) was added dropwise thereto with stirring. Exothermic reaction started immediately, and the temperature reached to 65° C. and then decreased. After dropping for about 15 min, the mixture was stirred at 55° C. for 4.5 hr. The reaction solution was concentrated, and water (300 ml) was added thereto. The mixture was extracted with chloroform (200 ml) twice. The extract was washed with saturated brine, dehydrated with anhydrous sodium sulfate and concentrated to give the title compound as a brown oil (83.62 g, yield 98.1%).

2) 2-Chloro-5,5-dimethyl-4-(1-naphthyl)-1,3,2-dioxaphosphorinane 2-oxide 2,2-Dimethyl-1-(1-naphthyl)-1,3-propanediol (83.6 g, 0.363 mol) and triethylamine (103.0 g, 1.018 mol) were dissolved in dichloromethane (300 ml). Phosphorus oxychloride (55.4 g, 0.361 mol) dissolved in dichloromethane (80 ml) was added dropwise to the solution above under cooling (2 to 4° C.) and with stirring for 1.5 hr. The solution was stirred at the same temperature for 1 hr, and water (150 ml) was added thereto to partition. The organic layer was washed with saturated brine, dried over anhydrous sodium sulfate and concentrated under reduced pressure. To the obtained dark brown oil was added diethylether (100 ml) and diisopropylether (100 ml) and the mixture was stirred thoroughly and then ice-cooled for 1 hr. The upper layer containing a large amount of unreacted 1-naphthoaldehyde was removed by decantation and the under layer was concentrated to give the title compound as a black tar (76.1 g, yield 67.8%).

3) 2-Hydroxy-5,5-dimethyl-4-(1-naphthyl)-1,3,2-dioxaphosphorinane 2-oxide

Sodium hydroxide (29.4 g, 0.735 mol) was dissolved in water (300 ml). To the solution was added 2-chloro-5,5-dimethyl-4-(1-naphthyl)-1,3,2-dioxaphosphorinane 2-oxide (76.1 g, 0.245 mol) little by little, with stirring and heating at 100° C. The addition was completed for 35 min, and the solution was further stirred for 20 min. The reaction solution was cooled to 55° C., which resulted in precipitation of a large amount of crystals. Under stirring, concentrated hydrochloric acid (73 ml) was added to the mixture to adjust the mixture to acidic, and the mixture solidified and turned into powder by leaving it for about 1 hr. To the powder was added ether (100 ml), and the mixture was stirred and filtered. The obtained crystals were washed alternately with water and ether and dried to give the title compound as pale ocher crystals having the melting point of 216 to 217° C. (41.23 g, yield 57.6%).

$^1$H-NMR (DMSO-d$_6$) δ: 0.64 (3H, s), 1.04 (3H, s), 3.94 (1H, dd, J=11.0 Hz, 24.9 Hz), 4.48 (1H, d, J=11.0 Hz), 6.21 (1H, s), 7.50-7.64 (4H, m), 7.92-8.01 (2H, m), 8.29 (1H, d, J=13.0 Hz)

4) Optical resolution of (±)-2-hydroxy-5,5-dimethyl-4-(1-naphthyl)-1,3,2-dioxaphosphorinane 2-oxide 2-Hydroxy-5,5-dimethyl-4-(1-naphthyl)-1,3,2-dioxaphosphorinane 2-oxide (racemate, 40.0 g, 0.137 mol) and (R)—(−)-(p-hydroxyphenyl) glycine (22.9 g, 0.137 mol) were added to ethanol (600 ml) and water (180 ml) and stirred with heating at 80° C. A small amount of insoluble substance was filtered off, and the filtrate was left in a refrigerator overnight, and the crystals of the precipitated diastereomeric salt was collected by filtration. (filtrate A) The crystals were stirred in ethanol with heating, ice-cooled and collected by filtration to give crystals (24.0 g). The crystals were suspended in water (170 ml), and 36% hydrochloric acid (23 ml) was added thereto and stirred for 3 hr for decomposition. The crystals were filtered off, washed with water and dried under reduced pressure at 50° C. to give crystals (16.4 g).

The crystals were added to 3.5% hydrochloric acid (250 ml) again and stirred for 1 hr. The crystals were collected by filtration and washed thoroughly with water to give crystals (12.1 g). The obtained crystals were dissolved in ethanol (500 ml) and decolorized with active carbon. Ethanol (about 300 ml) was then distilled off from the solution, and the residue was ice-cooled and the precipitated crystals were collected by filtration to give the (−) form as colorless crystals having the melting point of 207 to 208° C. (8.83 g, yield 44.2%). As a result of the HPLC analysis (condition B), the excess percentage of the enantiomer was 99.6% ee.

$[α]_D^{20}$=−62.0° (c=0.5, MeOH) Elemental analysis (for C$_{15}$H$_{17}$O$_4$P) Calcd. C, 61.64%; H, 5.89%; Found. C, 61.58%; H, 6.06% $^1$H-NMR (DMSO-d$_6$) δ: 0.64 (3H, s), 1.04 (3H, s), 3.95 (1H, dd, J=11.0 Hz, 24.9 Hz), 4.47 (1H, d, J=11.0 Hz), 6.21 (1H, s), 7.52-7.63 (4H, m), 7.94-7.98 (2H, m), 8.28 (1H, d, J=8.0 Hz)

The filtrate A was evaporated to dryness and the residual substance was stirred in ethanol (150 ml) with heating and ice-cooled, and the precipitated crystals (4.57 g) were filtered off. The filtrate was concentrated and ice-cooled. The further precipitated crystals (1.26 g) were filtered off and the filtrate was concentrated. To the dark brown oil was added water (200 ml) and 36% hydrochloric acid (35 ml) for decomposition, and the precipitated crystals were filtered off and washed with water to give crystals containing a large quantity of (+) form (20.79 g). The obtained crystals were dissolved in ethanol (250 ml) with heating. (R)—(+)-1-(1-Naphthyl)ethylamine (12.18 g, 0.071 mol) dissolved in ethanol (50 ml) was added to the above solution and stirred at 80° C. for 2 hr to form hardly soluble crystals of the diastereomeric salt. The solution were left under room temperature for 2 hr and then in a refrigerator overnight, the precipitated crystals were collected by filtration and washed with ethanol to give crystals (22.47 g). The filtrate was concentrated and ice-cooled to give the second crystals (3.14 g) further. These crystals were combined and stirred in ethanol (400 ml) with heating at 80° C. for 45 min and ice-cooled for 4 hr, and the precipitated crystals were collected by filtration. The obtained crystals were heated in ethanol (300 ml), ice-cooled and collected by filtration to give crystals having the melting point of 250 to 252° C. (decomposed, 16.19 g).

$[α]_D^{20}$=+31.2° (c=0.5, MeOH)

The crystals were suspended in water (120 ml), and concentrated hydrochloric acid (15 ml) was added thereto, and the mixture was stirred for 4 hr for decomposition. The crystals were collected by filtration and washed with water. The crystals were stirred again with water (120 ml) and 36% hydrochloric acid (15 ml) for 1 hr, filtered and washed thoroughly with water. The crystals were recrystallized from ethanol twice to give the (+)-form as colorless crystals having the melting point of 205.5 to 206.5° C. (2.24 g, yield 11.2%). As a result of HPLC analysis (condition B), the excess percentage of the enantiomer was >99.9% ee.

$[α]_D^{20}$=+62.2° (c=0.5, MeOH)

Reference Example 9

2-Hydroxy-5,5-dimethyl-4-(2-naphthyl)-1,3,2-dioxaphosphorinane 2-oxide 1) 2,2-Dimethyl-1-(2-naphthyl)-1,3-propanediol 2-Naphthoaldehyde (26.0 g, 0.167 mol) and isobutylaldehyde (24.0 g, 0.33 mol) were dissolved in ethanol (50 ml) with heating. 85% Potassium hydroxide (11.0 g, 0.167 mol) dissolved in ethanol (150 ml) was added dropwise to the above solution with stirring. Exothermic reaction started immediately, and the temperature reached to 51° C. and then decreased. After the dropping was completed for about 10 min, the solution was stirred at 55 to 60° C. for 4 hr. The reaction solution was concentrated under reduced pressure, and water (150 ml) was added thereto and the mixture was extracted with chloroform (100 ml) twice. The extract was washed with saturated brine, dehydrated with anhydrous sodium sulfate and concentrated to give the title compound as a brown oil (34.86 g, yield 91.0%).

2) 2-Chloro-5,5-dimethyl-4-(2-naphthyl)-1,3,2-dioxaphosphorinane 2-oxide 2,2-Dimethyl-1-(2-naphthyl)-1,3-propanediol (34.86 g, (0.151 mol) and triethylamine (42.9 g, 0.424 mol) were dissolved in dichloromethane (200 ml). Phosphorus oxychloride (24.3 g, 0.158 mol) dissolved in dichloromethane (50 ml) was added dropwise to the above solution under cooling to 1 to 4° C. with stirring for 1 hr 40 min. The solution was stirred at the same temperature for 1 hr, and water (60 ml) was added thereto to partition the solution. The organic layer was washed with saturated brine, dried over anhydrous sodium sulfate and concentrated under reduced pressure. To the obtained dark brown oil was added ether (50 ml) and the mixture was stirred thoroughly and left at room temperature overnight. The solidified reaction product was pulverized, filtered, washed with ether and dried to give the title compound (38.62 g, yield 82.1%).

$^1$H-NMR (CDCl$_3$) δ: 0.91 (3H, s), 1.14 (3H, s), 3.87-4.50 (2H, m), 5.46 (1H, d, J=2.6 Hz), 7.35-7.91 (7H, m)

3) 2-Hydroxy-5,5-dimethyl-4-(2-naphthyl)-1,3,2-dioxaphosphorinane 2-oxide

Sodium hydroxide (14.9 g, 0.373 mol) was dissolved in water (150 ml). To this solution was added little by little 2-chloro-5,5-dimethyl-4-(2-naphthyl)-1,3,2-dioxaphosphorinane-2-one (38.6 g, 0.124 mol) with heating to 100 to 102° C. and stirring for 30 min. The solution was stirred at the same temperature for 20 min, and the reaction solution was cooled to 45° C. Concentrated hydrochloric acid (37 ml) was added thereto to adjust the solution to acidic. The solution was stirred at 15° C. for 30 min. The crystals were collected by filtration, washed with water and then ether, and dried under reduced pressure at 60° C. to give the title compound as pale ocher crystals having the melting point of 237 to 238° C. (33.87 g, yield 93.2%).

$^1$H-NMR (DMSO-$d_6$) δ: 0.76 (3H, s), 0.95 (3H, s), 3.93 (1H, dd, J=11.0 Hz, 24.7 Hz), 4.23 (1H, d, J=11.0 Hz), 5.43 (1H, s), 7.46-7.59 (3H, m), 7.82-7.98 (4H, m)

4) Optical resolution of (±)-2-hydroxy-5,5-dimethyl-4-(2-naphthyl)-1,3,2-dioxaphosphorinane 2-oxide 2-Hydroxy-5,5-dimethyl-4-(2-naphthyl)-1,3,2-dioxaphosphorinane 2-oxide (racemate, 31.4 g, 0.107 mol) and (R)—(+)-1-(p-tolyl)ethylamine (14.53 g, 0.107 mol) were dissolved in ethanol (350 ml) with heating. The solution was stirred at room temperature for 1 hr and under ice-cooling for 2 hr, and left in a refrigerator overnight to precipitate a diastereomeric salt of the (−) form. This was collected by filtration and washed with ethanol to give crystals (18.42 g), (the filtrate A). A serial operation in which the crystals were heated with ethanol, cooled and collected by filtration, was repeated to give crystals having the melting point of 232 to 236° C. (14.54 g).

$[α]_D^{20}$=−43.4° (c=0.5, MeOH)

The crystals were suspended in water (100 ml), and 36% hydrochloric acid (14 ml) was added thereto and stirred for 7 hr for decomposition. The crystals were collected by filtration, washed with water, dried under reduced pressure 50° C., and recrystallized from ethanol (2 L) to give the (−)-form as colorless crystals having the melting point of 210 to 211° C. (7.33 g, yield 46.7%). As a result of HPLC analysis (condition B), the excess percentage of enantiomer was>99.9% ee.

$[α]_D^{20}$=−74.0° (c=0.2, MeOH) Elemental analysis (for $C_{15}H_{17}O_4P$) Calcd. for C, 61.64%; H, 5.89%; Found. C, 61.58%; H, 5.97% $^1$H-NMR (DMSO-$d_6$) δ: 0.76 (3H, s), 0.95 (3H, s), 3.94 (1H, dd, J=11.0 Hz, 24.7 Hz), 4.23 (1H, d, J=11.0 Hz), 5.44 (1H, s), 7.46-7.56 (3H, m), 7.86 (1H, s), 7.92-7.98 (3H, m)

The filtrate A was evaporated to dryness and the residue was added to water (200 ml) and 36% hydrochloric acid (30 ml), and stirred for 7 hr for decomposition to give crystals containing a large amount of (+)-form (18.9 g). These crystals were heated with (S)-(−)-1-(p-tolyl)ethylamine (8.7 g, 0.0647 mol) in ethanol (350 ml) at 80° C. for 30 min, and the solution was stirred for 3 hr under ice-cooling, and the crystals were collected by filtration. The crystals were added to ethanol (150 ml) again, and the mixture was stirred at 80° C. for 0.5 hr and ice-cooled. The crystals were collected by filtration to give crystals having the melting point of 230 to 232° C. (13.59 g).

$[α]_D^{20}$=+46.4° (c=0.5, MeOH)

The crystals were decomposed with water (100 ml) and 36% hydrochloric acid (13 ml) to give white crystals (9.84 g). These crystals were recrystallized from methanol (1.8 L), stirred in ethanol (200 ml) at 80° C. for 15 min, ice-cooled and collected by filtration to give the (+)-form as colorless crystals having the melting point of 211 to 212° C. (8.03 g, yield 51.1%). As a result of HPLC analysis (condition B), the excess percentage of enantiomer was >99.9% ee.

$[α]_D^{20}$=+75.5° (c=0.2, MeOH) Elemental analysis (for $C_{15}H_{17}O_4P$) Calcd. for C, 61.64%; H, 5.89%; Found. C, 61.67%; H, 6.15% $^1$H-NMR (DMSO-$d_6$) δ: 0.76 (3H, s), 0.95 (3H, s), 3.94 (1H, dd, J=11.0 Hz, 24.7 Hz), 4.23 (1H, d, J=11.0 Hz), 5.44 (1H, s), 7.46-7.56 (3H, m), 7.86 (1H, s), 7.92-7.98 (3H, m)

INDUSTRIAL APPLICABILITY

According to the production method of the present invention, a synthetic intermediate for an optically active 2,3-dihydrobenzofuran compound that is useful itself as a medicine as well as the other medicines for preventing or treating nerve degenerative diseases and the like can be conveniently and industrially advantageously produced.

The invention claimed is:

1. A process for preparing a compound represented by the formula:

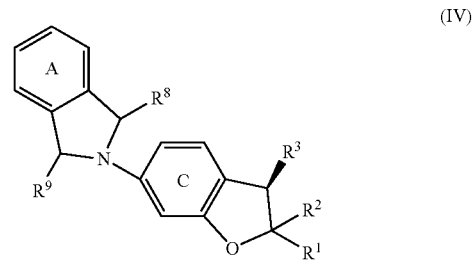

(IV)

wherein $R^1$ and $R^2$ are each a hydrogen atom or an optionally substituted hydrocarbon group, $R^3$ is an optionally substituted aromatic group, ring A is an optionally substituted benzene ring, $R^8$ and $R^9$ are each a hydrogen atom, ring C is a benzene ring optionally having substituent besides the amino group, or a salt thereof, comprising optically resolving a 2,3-dihydrobenzofuran compound represented by the formula:

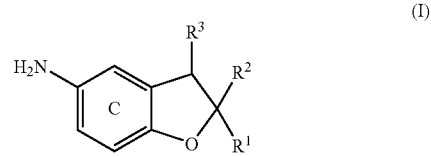

(I)

wherein the symbols are as defined above, or a salt thereof with an optically active acidic compound to give the compound represented by the formula:

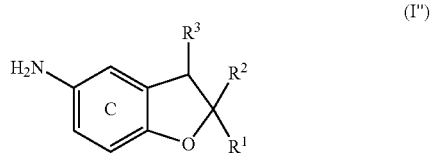

(I'')

wherein the symbols are as defined above, or a salt thereof, and reacting the obtained compound (I'') with a compound represented by the formula:

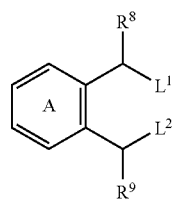 (III)

wherein L¹ and L² are each a chlorine atom hydroxy and the ring A, R⁸, and R⁹ are as defined above, or a salt thereof, optionally in the presence of a base.

2. The process according to claim 1, wherein (R)—(+)-5,6-dimethoxy-2-[2,2,4,6,7-pentamethyl-3-(4-methylphenyl)-2,3-dihydro-1-benzofuran-5-yl]isoindoline, (R)—(+)-5,6-dimethoxy-2-[2,2,4,6,7-pentamethyl-3-(1-methylethylphenyl)-2,3-dihydro-1-benzofuran-5-yl]isoindoline or (R)—(+)-5,6-dimethoxy-2-[2,2,4,6,7-pentamethyl-3-(4-bromophenyl)-2,3-dihydro-1-benzofuran-5-yl]isoindoline, or a salt thereof is produced.

\* \* \* \* \*